(12) United States Patent
Ghosh et al.

US007060864B2

(10) Patent No.: US 7,060,864 B2
(45) Date of Patent: Jun. 13, 2006

(54) TOLUENE METHYLATION PROCESS

(75) Inventors: Ashim Kumar Ghosh, Houston, TX (US); Pamela Harvey, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 131 days.

(21) Appl. No.: 10/675,780

(22) Filed: Sep. 30, 2003

(65) Prior Publication Data

US 2005/0070749 A1 Mar. 31, 2005

(51) Int. Cl.
C07C 2/66 (2006.01)
(52) U.S. Cl. ..................................... 585/467
(58) Field of Classification Search ................ 585/467
See application file for complete search history.

(56) References Cited

U.S. PATENT DOCUMENTS

| | | |
|---|---|---|
| 3,702,886 A | 11/1972 | Argauer et al. |
| 3,965,207 A | 6/1976 | Weinstein |
| 4,278,827 A | 7/1981 | Chu et al. |
| 4,548,914 A | 10/1985 | Chu |
| 4,590,321 A | 5/1986 | Chu |
| 4,623,530 A | 11/1986 | Cullo et al. |
| 4,623,533 A | 11/1986 | Broecker et al. |
| 4,638,106 A | 1/1987 | Pieters et al. |
| 4,665,251 A | 5/1987 | Chu |
| 4,670,616 A | 6/1987 | De Simone et al. |
| 4,673,767 A | 6/1987 | Nimry et al. |
| 4,694,114 A | 9/1987 | Chu et al. |
| 4,695,666 A | 9/1987 | Chao et al. |
| 4,695,667 A | 9/1987 | Sumitani et al. |
| 4,704,495 A | 11/1987 | Dessau |
| 4,716,135 A | 12/1987 | Chen |
| 4,721,827 A | 1/1988 | Cullo et al. |
| 4,727,209 A | 2/1988 | Chao |
| 4,746,763 A | 5/1988 | Kocal |
| 4,758,328 A | 7/1988 | Young |
| 4,761,513 A | 8/1988 | Steacy |
| 4,847,223 A | 7/1989 | Le Van Mao et al. |
| 4,861,930 A | 8/1989 | Cottrell et al. |
| 4,873,067 A | 10/1989 | Valyocsik et al. |
| 4,891,197 A | 1/1990 | Derouane et al. |
| 4,891,467 A | 1/1990 | Sikkenga |
| 4,902,406 A | 2/1990 | Valyocsik |
| 4,912,073 A | 3/1990 | Chu |
| 4,914,067 A | 4/1990 | Pellet et al. |
| 4,935,574 A | 6/1990 | D'Amore et al. |
| 4,962,255 A | 10/1990 | Fraenkel et al. |
| 4,973,781 A | 11/1990 | Valyocsik et al. |
| 5,041,402 A | 8/1991 | Casci et al. |
| 5,043,502 A | 8/1991 | Martindale et al. |
| 5,047,141 A | 9/1991 | Chu |
| 5,068,483 A | 11/1991 | Barthomeuf et al. |
| 5,094,995 A | 3/1992 | Butt et al. |
| 5,105,047 A | 4/1992 | Waller |
| 5,108,579 A | 4/1992 | Casci |
| 5,110,776 A | 5/1992 | Chitnis et al. |
| 5,124,299 A | 6/1992 | Waller |
| 5,171,921 A | 12/1992 | Gaffney et al. |
| 5,173,461 A | 12/1992 | Absil et al. |
| 5,178,748 A | 1/1993 | Casci et al. |
| 5,210,356 A | 5/1993 | Shamshoum et al. |
| 5,227,558 A | 7/1993 | Shamshoum et al. |
| 5,231,064 A | 7/1993 | Absil et al. |
| 5,233,102 A | 8/1993 | Butt et al. |
| 5,246,688 A | 9/1993 | Faust et al. |
| 5,248,841 A | 9/1993 | Young |
| 5,254,767 A | 10/1993 | Dwyer |
| 5,254,770 A | 10/1993 | Olson et al. |
| 5,294,578 A | 3/1994 | Ho et al. |
| 5,315,033 A | 5/1994 | Butt et al. |
| 5,318,696 A | 6/1994 | Kowalski |
| 5,321,183 A | 6/1994 | Chang et al. |
| 5,336,478 A | 8/1994 | Dwyer et al. |
| 5,336,824 A | 8/1994 | Shamshoum et al. |
| 5,345,021 A | 9/1994 | Casci et al. |
| 5,348,643 A | 9/1994 | Absil et al. |
| 5,349,113 A | 9/1994 | Chang et al. |
| 5,365,003 A | 11/1994 | Chang et al. |
| 5,366,948 A | 11/1994 | Absil et al. |
| 5,367,100 A | 11/1994 | Gongwei et al. |
| 5,371,307 A | 12/1994 | Guth et al. |
| 5,378,670 A | 1/1995 | Kumar |
| 5,380,690 A | 1/1995 | Zhicheng et al. |
| 5,385,718 A | 1/1995 | Casci et al. |
| 5,387,732 A | 2/1995 | Shamshoum et al. |
| 5,399,336 A | 3/1995 | Guth et al. |
| 5,430,212 A | 7/1995 | Butt et al. |
| 5,430,213 A | 7/1995 | Hendriksen et al. |
| 5,446,234 A | 8/1995 | Casci et al. |
| 5,455,213 A | 10/1995 | Chang et al. |
| 5,456,821 A | 10/1995 | Absil et al. |
| 5,464,799 A | 11/1995 | Casci et al. |

(Continued)

OTHER PUBLICATIONS

Kaeding, W.W., et al., Selective Alkylation of Toluene to Produce para-Xylene, Journal of Catalysis 67, 1981, pp. 159-174, no month.

(Continued)

Primary Examiner—Elizabeth D. Wood
(74) Attorney, Agent, or Firm—Jim D. Wheelington; Grady K. Bergen

(57) ABSTRACT

A method of preparing a xylene product is carried out by providing a reactor containing a non-steamed, phosphorus-treated ZSM-5-type zeolite catalyst. The catalyst is contacted with a toluene/methanol feed and a cofeed of hydrogen under reactor conditions suitable for the methylation of toluene. Water is introducing into the reactor during the methylation reaction under conditions that provide substantially no structural aluminum loss of the catalyst from such introduction of water.

21 Claims, 6 Drawing Sheets

U.S. PATENT DOCUMENTS

| | | |
|---|---|---|
| 5,475,179 A | 12/1995 | Chang et al. |
| 5,498,814 A | 3/1996 | Chang et al. |
| 5,503,818 A | 4/1996 | Nicolaides |
| 5,516,736 A | 5/1996 | Chang et al. |
| 5,523,510 A | 6/1996 | Pellet et al. |
| 5,534,239 A | 7/1996 | Fajula et al. |
| 5,536,894 A | 7/1996 | Degnan et al. |
| 5,541,146 A | 7/1996 | Chang et al. |
| 5,561,095 A | 10/1996 | Chen et al. |
| 5,563,310 A | 10/1996 | Chang et al. |
| 5,569,805 A | 10/1996 | Beck et al. |
| 5,571,768 A | 11/1996 | Chang et al. |
| 5,573,746 A | 11/1996 | Chen |
| 5,576,256 A | 11/1996 | Monque et al. |
| 5,607,888 A | 3/1997 | Chang et al. |
| 5,607,890 A | 3/1997 | Chen et al. |
| 5,646,314 A | 7/1997 | Crocco et al. |
| 5,648,580 A | 7/1997 | Chen et al. |
| 5,658,454 A | 8/1997 | Absil et al. |
| 5,675,047 A | 10/1997 | Beck et al. |
| 5,689,024 A | 11/1997 | Schmitt |
| 5,698,756 A | 12/1997 | Beck et al. |
| 5,780,563 A | 7/1998 | Chen et al. |
| 5,789,335 A | 8/1998 | Chen et al. |
| 5,811,613 A | 9/1998 | Bhat et al. |
| 5,833,840 A | 11/1998 | Absil et al. |
| 5,847,255 A | 12/1998 | Ghosh et al. |
| 5,902,919 A | 5/1999 | Chen et al. |
| 5,905,051 A | 5/1999 | Wu et al. |
| 5,907,073 A | 5/1999 | Ghosh |
| 5,922,922 A | 7/1999 | Harris et al. |
| 5,925,586 A | 7/1999 | Sun |
| 5,939,597 A | 8/1999 | Dessau et al. |
| 5,951,963 A | 9/1999 | He et al. |
| 5,955,641 A | 9/1999 | Chen et al. |
| 5,990,031 A | 11/1999 | Ghosh |
| 5,994,603 A | 11/1999 | Mohr et al. |
| 6,034,283 A | 3/2000 | Ban et al. |
| 6,040,257 A | 3/2000 | Drake et al. |
| 6,046,128 A | 4/2000 | Kisen et al. |
| 6,047,544 A | 4/2000 | Yamamoto et al. |
| 6,048,816 A | 4/2000 | Brown et al. |
| 6,057,485 A | 5/2000 | Merrill et al. |
| 6,060,633 A | 5/2000 | Chen et al. |
| 6,074,975 A | 6/2000 | Yao et al. |
| 6,080,303 A | 6/2000 | Cao et al. |
| 6,080,698 A | 6/2000 | Zhang et al. |
| 6,083,865 A | 7/2000 | Drake et al. |
| 6,090,274 A | 7/2000 | Wu et al. |
| 6,090,991 A | 7/2000 | Butler et al. |
| 6,096,938 A | 8/2000 | Ghosh |
| 6,100,437 A | 8/2000 | Koehl et al. |
| 6,124,227 A | 9/2000 | Yao et al. |
| 6,150,293 A | 11/2000 | Verduijn et al. |
| 6,156,949 A | 12/2000 | Brown et al. |
| 6,160,191 A | 12/2000 | Smith et al. |
| 6,187,982 B1 | 2/2001 | Beck et al. |
| 6,211,104 B1 | 4/2001 | Shi et al. |
| 6,217,748 B1 | 4/2001 | Hatanaka et al. |
| 6,222,084 B1 | 4/2001 | Ghosh et al. |
| 6,251,263 B1 | 6/2001 | Hatanaka et al. |
| 6,268,305 B1 | 7/2001 | Butler et al. |
| 6,294,493 B1 | 9/2001 | Strohmaier et al. |
| 6,300,535 B1 | 10/2001 | van den Berge et al. |
| 6,306,790 B1 | 10/2001 | Rodriguez et al. |
| 6,342,153 B1 | 1/2002 | Guan et al. |
| 6,388,156 B1 | 5/2002 | Ou et al. |
| 6,395,664 B1 | 5/2002 | Boehner et al. |
| 6,399,530 B1 | 6/2002 | Chen et al. |
| 6,417,421 B1 | 7/2002 | Yao |
| 6,423,879 B1 | 7/2002 | Brown et al. |
| 6,444,610 B1 | 9/2002 | Yamamoto |
| 6,459,006 B1 | 10/2002 | Ou et al. |
| 6,469,095 B1 | 10/2002 | Gareiss et al. |
| 6,503,862 B1 | 1/2003 | Yamamoto |
| 6,504,072 B1 | 1/2003 | Brown et al. |
| 6,504,074 B1 | 1/2003 | Verduijn et al. |
| 6,506,954 B1 | 1/2003 | Brown et al. |
| 6,518,213 B1 | 2/2003 | Yamamoto et al. |
| 6,548,725 B1 | 4/2003 | Froment et al. |
| 6,566,293 B1 | 5/2003 | Vogt et al. |
| 6,589,901 B1 | 7/2003 | Yamamoto |
| 6,613,708 B1 | 9/2003 | Ou et al. |
| 6,613,951 B1 | 9/2003 | Brown et al. |
| 6,642,426 B1 | 11/2003 | Johnson et al. |
| 6,689,929 B1 | 2/2004 | Williams et al. |
| 6,699,811 B1 | 3/2004 | Mohr et al. |
| 6,723,297 B1 | 4/2004 | Chen et al. |
| 6,726,834 B1 | 4/2004 | Quesada et al. |
| 6,770,251 B1 | 8/2004 | Yoshikawa |
| 6,773,694 B1 | 8/2004 | Lesch et al. |
| 6,799,089 B1 | 9/2004 | Toulhoat |
| 6,811,684 B1 | 11/2004 | Mohr et al. |
| 6,812,181 B1 | 11/2004 | van der Berge et al. |

OTHER PUBLICATIONS

Hibino, T., et al., Shape-Selectivity Over HZSM-5 Modified by Chemical Vapor Deposition of Silicon Alkoxide, Journal of Catalysis 128, 1991, pp. 551-558, no month.

Yashima, T., et al., Selective Formation of p-Xylene by Alkylation of Toluene with Methanol on ZSM-5 Type Zeolites, Stud. Surf. Sci. Catal., 1981, 7, pp. 739-751, no month.

Sayed, M. B., et al., The Effect of Modification with Boron on the Catalytic Activity and Selectivity of HZSM-5, Journal of Catalysis 101, 1986, pp. 43-55, no month.

Kim, J.-H, et al., Generation of Shape-Selectivity of p-Xylene Formation in the Synthesized ZSM-5 Zeolites, Journal of Catalysis 173, 1998, pp. 433-439, no month.

Vinek, H., et al., Production and Reactions of Xylenes over H-ZSM-5, Journal of Molecular Catalysis, 64, 1991, pp. 23-39, no month.

Chen, N.Y., Reactions of Mixtures of Toluene and Methanol Over ZSM-5, Journal of Catalysis 114, 1988, pp. 17-22, no month.

Young, L.B., et al., Shape Selective Reactions with Zeolite Catalysts, Journal of Catalysis 76, 1982, pp. 418-432, no month.

Nirula, S.C., Para-Xylene From Toluene and Methanol, Process Economics Program, 1983, pp. 1-23, SRI International, Menlo Park, CA, no month.

Wang, I., et al., Para-selectivity of Diaklybenzenes over Modified HZSM-5 by Vapour Phase Deposition of Silica, Applied Catalysis, 54, 1989, 257-266, no month.

Das, J., et al., Ethylbenzene Dealkylation and Realkylation over Pore Size Regulated MFI Zeolite, Ind. Eng. Chem. Res., 32, 1993, pp. 2525-2529, no month.

Kim, J.-H., et al., Para-selectivity of Metallosilicates with MFI Zeolite Structure Zeolites, vol. 11, 1991, pp. 59-63, no month.

Kim, J.-H., et al., Preparation of Highly Para-selective Metallosilicate Catalysts for Alkylation of Ethylbenzene with Ethanol, Applied Catalysis A:100, 1993, pp. 27-36, no month.

TOLUENE METHYLATION PROCESS

TECHNICAL FIELD

The invention relates generally to the alkylation of aromatic compounds.

BACKGROUND

Para-xylene is a valuable substituted aromatic compound because of its great demand for its oxidation to terephthalic acid, a major component in forming polyester fibers and resins. It can be commercially produced from hydrotreating of naphtha (catalytic reforming), steam cracking of naphtha or gas oil, and toluene disproportionation.

Alkylation of toluene with methanol, which is also known as toluene methylation, has been used in laboratory studies to produce para-xylene. Toluene methylation has been known to occur over acidic catalyst, particularly over zeolite or zeolite-type catalyst. In particular, ZSM-5-type zeolite, zeolite Beta and silicaaluminophosphate (SAPO) catalysts have been used for this process. Generally, a thermodynamic equilibrium mixture of ortho (o)-, meta (m)- and para (p)-xylenes can be formed from the methylation of toluene, as is illustrated by the reaction below.

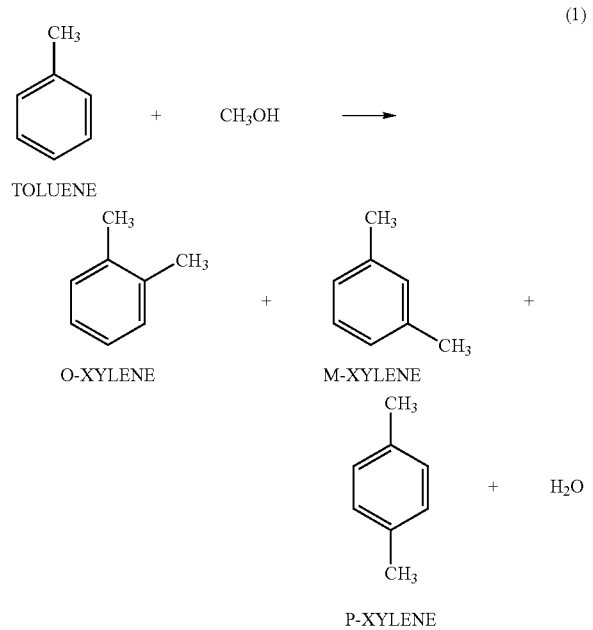

Thermodynamic equilibrium compositions of o-, m-, and p-xylenes may be around 25, 50 and 25 mole %, respectively, at a reaction temperature of about 500° C. Such toluene methylation may occur over a wide range of temperatures, however. Byproducts such as C9+ and other aromatic products can be produced by secondary alkylation of the xylene product.

Para-xylene can be separated from mixed xylenes by a cycle of adsorption and isomerization. Such cycle may have to be repeated several times because of the low isomeric concentration in the equilibrium mixture. A high purity grade (99+%) p-xylene is desirable for its oxidation to terephthalic acid. The production cost for such a high purity grade p-xylene can be very high, however. A different method that employs crystallization techniques can be used and may be less expensive where the concentration of p-xylene is around 80% or higher in the initial xylene product. Thus, higher than equilibrium concentrations of p-xylene may be desirable.

A significantly higher amount of p-xylene can be obtained in toluene methylation reaction if the catalyst has shape selective properties. Shape selective properties can be obtained in modified zeolite catalysts by narrowing zeolite pore opening size, inactivation of the external surface of the zeolite or controlling zeolite acidity. Toluene methylation may occur over modified ZSM-5 or ZSM-5-type zeolite catalyst giving xylene products containing significantly greater amounts of p-xylene than the thermodynamic concentration.

In Kaeding, et al, *Selective Alkylation of Toluene with Methanol to Produce para-Xylene,* Journal of Catalysis, Vol. 67, pp. 159–174 (1981), a procedure of making a ZSM-5 catalyst by incorporating 5% phosphorus was described in which the catalyst was impregnated with a solution of diphenylphosphinous acid in toluene. The ZSM-5 catalyst thus modified showed toluene methylation activity with 84–90% para isomer in the xylene product. In another procedure, a catalyst was modified by incorporating 8.51% phosphorus from an aqueous phosphoric acid reagent. The catalyst showed p-xylene selectivity as high as 97%, however, the catalyst showed a decreasing activity within hours due to coke deposition.

BRIEF DESCRIPTION OF THE DRAWINGS

For a more complete understanding of the present invention, reference is now made to the following descriptions taken in conjunction with the accompanying figures, in which.

DETAILED DESCRIPTION

Figure 1:
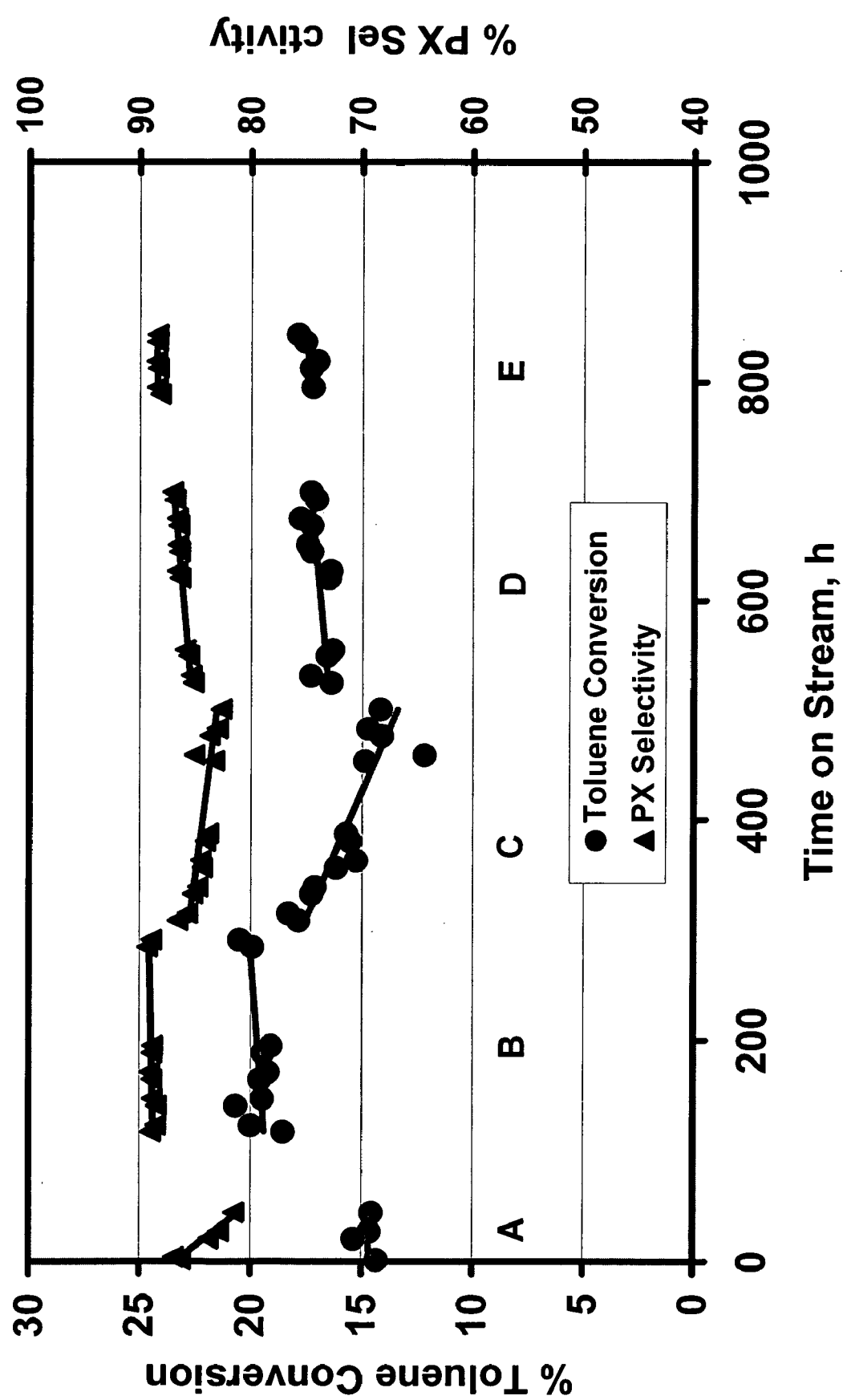
FIG. 1 is a plot of toluene conversion and para-xylene selectivity over time for the toluene methylation reaction of Example 4.

Modification of ZSM-5-type zeolite catalysts with phosphorus-containing compounds has been shown to yield significantly greater amounts of p-xylene than the thermodynamic equilibrium value in toluene methylation using unmodified catalysts. Such modification has been shown to provide selectivity for p-xylenes of greater than 80%. Although such phosphorus-treated ZSM-5 catalysts may have a high selectivity for p-xylene, they tend to deactivate at a very fast rate, for example, the catalyst may lose greater than 50% of its initial activity within a day. This may possibly be due to coke deposition on the catalyst.

As used herein, the expression "ZSM-5-type" is meant to refer to those zeolites that are isostructurally the same as ZSM-5 zeolites. Additionally, the expressions "ZSM-5" and "ZSM-5-type" may also be used herein interchangeably to encompass one another and should not be construed in a limiting sense. As used herein, catalytic activity can be expressed as the % moles of toluene converted with respect to the moles of toluene fed and can be defined as:

$$\text{Mole \% Toluene Conversion} = [(T_i - T_o)/T_i] \times 100 \quad (2)$$

where, $T_i$ is the number of moles of toluene fed and $T_o$ is the number of moles toluene unreacted. As used herein, selectivity for total xylenes may be expressed as:

$$\text{Mole \% Total Xylene Selectivity} = [X_{tx}/(T_i - T_o)] \times 100 \quad (3)$$

where, $X_{tx}$ is the number of moles of total (o-, m- or p-) xylenes in the product. As used herein, selectivity for p-xylene may be expressed as:

$$\text{Mole \% p-Xylene Selectivity} = (X_p/X_{tx}) \times 100 \quad (4)$$

where, $X_p$ is the number of moles of p-xylene.

It has been discovered that by introducing water or steam into the reactor as cofeed along with the toluene/methanol feed during the alkylation reaction, catalyst activity and selectivity can be increased, stabilized or their rate of decrease reduced when using non-steamed, phosphorus-treated ZSM-5-type zeolite catalyst. As used herein, "non-steamed," as it refers to the zeolite catalyst, is meant to include zeolite catalyst that has not been treated or subjected to high temperature steam (i.e. greater than 950° C.) to effect structural changes of the catalyst prior to its use in any alkylation or methylation reactions.

The water or stream used for the methylation reaction may be introduced with or without hydrogen as cofeed with the hydrocarbon feed (HC=toluene+methanol) to the reactor during the start up of the alkylation reaction or it may be introduced subsequent to initial start up. The invention has particular application in toluene methylation reactions using the described catalysts that have high selectivity for p-xylene. In particular, selectivity for p-xylene may be from about 80%, 85%, 90% or 95% or more by total moles of xylene. Unless stated otherwise, all percentages for conversion and selectivity are in mole %.

The ZSM-5 zeolite catalysts and their preparation are described in U.S. Pat. No. 3,702,886, which is herein incorporated by reference. In the present invention, the ZSM-5 zeolite catalyst may include those having a silica/alumina molar ratio of from 25 to 300, more particularly from about 30 to about 280 prior to modification.

The ZSM-5 may be modified by treating with phosphorus (P)-containing compounds. Such phosphorus-containing compounds may include phosphonic, phosphinous, phosphorus and phosphoric acids, salts and esters of such acids and phosphorous halides. In particular, phosphoric acid ($H_3PO_4$) and ammonium hydrogen phosphate (($NH_4$)$_2HPO_4$) may be used as the phosphorus-containing compound to provide a catalyst for toluene methylation with shape selective properties to give high p-xylene concentration. Such modified catalysts may contain phosphorus in an amount of from about 0.01 to about 0.15 g P/g zeolite, more particularly from about 0.02 to about 0.13 g P/g zeolite. The phosphorus-modified zeolite may be calcined at temperature of about 500 to 570° C. The catalyst may have a BET surface area of 170–200 m$^2$/g and pore volume in the range of 0.10–0.18 ml/g catalyst. The catalyst may have weak acidity showing broad peak(s) with peak maxima between 250° C. and 350° C., as characterized by ammonia temperature programmed desorption ($NH_3$-TPD) technique.

The modified zeolite catalyst may be bound with a binder such as alumina, clay, and silica. The bound catalyst may be calcined at a temperature between 450° C. and 570° C. These techniques for preparing the bound catalyst are well known in the art.

In carrying out the toluene methylation reaction, start up of the reaction may include particular short-term start-up conditions that may then be adjusted thereafter to run conditions, which may generally continue for extended periods of time. These start-up conditions may include an initial toluene/methanol feed to the reactor containing the phosphorus-treated ZSM-5 catalyst to provide an initial liquid hourly space velocity (LHSV) of from about 1 hr$^{-1}$ to about 90 hr$^{-1}$, more particularly from about 1 to about 70 hr$^{-1}$. The toluene and methanol feed may be premixed prior to introduction into the reactor as a single mixed feed stream. The feed may also contain small quantities of water, C9+aromatics and other compounds. The liquid hourly space velocities presented herein, however, are based upon a toluene/methanol feed without the inclusion of any other components. The toluene/methanol molar ratio in the feed can range from 0.5 to 10.0, more particularly 1.0 to 5.0. Additionally, an initial cofeed of hydrogen gas ($H_2$) is provided at a hydrogen/hydrocarbon ($H_2$/HC) molar ratio of less than about 10, more particularly from about 0.1 to about 8. Unless otherwise noted, all $H_2$/HC ratios presented herein are molar ratios. The reactor temperature used herein referred as catalyst bed inlet temperature and a reactor temperature between 400° C. and 700° C. is provided at start-up.

The water that is introduced to facilitate increased catalyst activity and selectivity may be introduced during the start-up of the reaction, but it may also be introduced after the initial start-up. In either case, liquid water may be added and vaporized prior to its mixing with hydrogen cofeed (if any) and hydrocarbon feed.

The reactor pressure may remain generally constant during both start-up and normal run stages. The reactor pressure may vary but typically ranges from about 10 to about 50 psig, more particularly from about 20 to about 50 psig.

The reaction may be carried out in a fixed bed, continuous flow-type reactor in a down flow mode. Single or multi reactors in series and/or parallel are suitable for carrying out the reaction. During start-up, the reactor temperature can be gradually increased. Initially, upon introduction of feed into the reactor, the reactor temperature may be about 200° C. or above. The temperature may then be increased to the final desired temperature. This temperature may be increased gradually at a rate of from about 1° C./min to about 10° C./min to provide a final start-up reactor temperature of from about 400° C. to about 700° C.

Such start-up conditions may be maintained for a certain period of time after which the conditions may be adjusted to "run conditions" for steady toluene conversion and selectivity to p-xylene. The use of different start-up conditions is described in the co-pending U.S. patent application Ser. No. 10/632,254, which is herein incorporated by reference. Such adjustments may include the reduction of hydrocarbon feed rate (i.e., reduction of LHSV) and an increase of hydrogen rate (i.e., an increase of $H_2$/HC molar ratio). The temperature may be maintained at from about 400° C. to about 700° C. during run conditions.

The water introduced into the reactor may be fed into the reactor at a ratio of from about 0.2 to more, and may be less than about 10 moles water per mole of hydrocarbons, more particularly, from about 0.3 to about 5, 6 or 7 moles water per mole of hydrocarbons. In certain instances, the water may be fed at a ratio of from about 0.2 to 1.2 moles water per mole of hydrocarbons, more particularly, from about 0.3 to about 0.8 mole water per mole of hydrocarbons. The addition of water (or steam) as cofeed may be done in combination with or without hydrogen cofeed. As evidenced from examples, the advantage of increased activity and selectivity due to steam cofeed can not be substituted by adding the same number of moles of hydrogen in the feed.

The water is fed into the reactor wherein the conditions are such that substantially no structural aluminum loss of the catalyst results due to the presence of such additional water within the reactor.

The following examples better serve to illustrate the invention.

EXAMPLES

The reactions in the following examples were carried out in a fixed bed, flow-type reactor in a downflow mode wherein the toluene and methanol were premixed prior to introduction into the reactor. Liquid water was added separately and was vaporized prior to its mixing with hydrocarbon feed and hydrogen gas, if any. ZSM-5 zeolite catalysts were treated using either phosphoric acid (Examples 1–11) or ammonium hydrogen phosphate (Example 12). The ZSM-5 zeolite catalyst initially utilized a $NH_4$-ZSM-5 zeolite powder having a silica/alumina ($SiO_2/Al_2O_3$) mole ratio of about 280 prior to phosphorus treatment. This was then calcined to form H-ZSM-5 zeolite. The ZSM-5 zeolite catalyst so modified was not subjected to any further modification such as steaming or dealumination.

Preparation of the ZSM-5 zeolite catalysts utilizing phosphoric acid was carried out by combining approximately 50 g of the $NH_4$-ZSM-5 zeolite powder and 100–150 ml of deionized water in a 400 ml beaker. This was then placed on a hot plate and the zeolite suspension was stirred using a magnetic stir bar. The suspension was maintained at a temperature of approximately 100° C. Phosphoric acid (15.8 g at 85% by weight in water) was then added dropwise to the beaker. Heating was continued until the water was completely evaporated. The modified zeolite was dried at about 110° C. in a muffle furnace for at least 4 hours. The modified zeolite was then calcined at 510 or 530° C. in air. The calcined zeolite was then crushed and sieved to 20/40 mesh. The final catalyst thus synthesized possessed the following properties: BET surface area about 190 $m^2/g$, pore volume about 0.139 ml/g, average pore diameter about 29 Å.

In Example 3, the phosphoric acid treated ZSM-5 zeolite catalyst utilized was bound with alumina. About 5.6 g alumina (boehmite crystals, also referred as pseudoboehmite) was peptized by vigorously mixing with about 2.0 g of nitric acid (70% in aqueous). About 22.4 g of modified ZSM-5 zeolite powder (described in preceding paragraph) was then mixed with the peptized alumina and made into a dough by mixing and spraying water. The dough was made into small pieces and was then calcined at a programmable temperature profile with a maximum temperature of 530° C. for at least for 6 h. The calcined catalyst was sized between 20 and 40 mesh.

For the ammonium hydrogen phosphate (AHP) treated ZSM-5 zeolite catalyst (Example 12), a slurry of the ammonium ion-exchanged ZSM-5 zeolite in deionized water was prepared. The slurry was then heated to about 80° C. and to this was added the AHP (0.24 g AHP/g of ZSM-5 powder). The mixture was then heated to approximately 100° C. in order to evaporate substantially all water. The resulting zeolite was then dried in an oven overnight at a temperature at about 90 to 120° C. The dried zeolite was then calcined in air at a temperature of about 530° C. No binder was used to form the catalyst. The modified ZSM-5 was sized to form a 20–40 mesh. The final catalyst thus synthesized possessed the following properties: BET surface area about 190 $m^2/g$, pore volume about 0.139 ml/g, average pore diameter about 29 Å.

In Examples 1–12, the reactor consisted of a stainless steel tube having an OD of approximately ½-inch. A catalyst charge, ranging from 0.5 ml to 6.0 ml, was placed within the tubular reactor at about its midpoint. Layers of inert material such as silicon carbide, SiC, were added to both ends of the catalyst bed. The feed was made by mixing toluene and methanol at a desired ratio. The feed was then pumped at a predetermined rate. Hydrogen gas was added to the feed at a predetermined rate to maintain a selected $H_2$/HC ratio. Liquid water was added at a predetermined rate and was vaporized prior to its mixing with hydrocarbon feed, and hydrogen gas (if any).

After more than 500 hours of use in the toluene methylation reaction using steam as cofeed (as described in Examples 4 and 12), the spent catalyst was removed from the reactor and the catalyst was decoked by burning coke in air at 510° C. The catalyst was then analyzed by magic angle spinning (MAS) solid state NMR spectroscopy for $^{27}Al$. As shown at the end of Example 12, the $^{27}Al$ NMR spectroscopic study suggests that no structural aluminum loss from the modified ZSM-5 zeolite occurred during the toluene methylation reaction in presence of steam cofeed.

Example 1

A catalyst charge of 3.0 ml was loaded in the reactor. The catalyst was dried at 200° C. under $H_2$ flow for at least 1 hour prior to feed introduction. The reactor pressure was maintained at about 20 psig. In this example, the start-up and run conditions were maintained the same. Toluene/methanol feed at a 2:1 mole ratio was introduced at a rate of about 3.09 ml/min giving a LHSV of about 62 $hr^{-1}$. The cofeed $H_2$ was used at a rate to give a $H_2$/HC mole ratio of about 0.1. Water was introduced with the feed at about 0.65 mole $H_2O$/mole HC feed. The run conditions and results are presented in Tables 1A and 1B below.

TABLE 1A

| Run Conditions | |
|---|---|
| Catalyst | Phosphoric Acid Treated ZSM-5, Non-Bound |
| Feed | 2:1 ratio |
| Start-up | LHSV 62, H2/HC = 0.1, T 450° C. |
| Normal run | Same as start-up |
| Water in feed | Started same time of HC feed |

TABLE 1B

| | Time on Stream, hour | | |
|---|---|---|---|
| | 2.2 | 3.2 | 4.2 |
| Cat Bed Inlet Temp, ° C. | 450 | 448 | 453 |
| Inlet Pressure, psig | 24 | 26 | 26 |
| LHSV[a] | 62 | 62 | 62 |
| H2, mole/mole HC Feed | 0.11 | 0.11 | 0.11 |
| H2O, mole/mole HC Feed | 0.65 | 0.65 | 0.65 |

TABLE 1B-continued

|  | Time on Stream, hour | | |
|---|---|---|---|
|  | 2.2 | 3.2 | 4.2 |
| Product Distribution, wt % | | | |
| C5– | 1.01 | 1.81 | 1.91 |
| Dimethylether | 0 | 0 | 0 |
| Methanol | 7.21 | 4.28 | 5.45 |
| Benzene | 0 | 0 | 0 |
| Toluene | 84.60 | 83.30 | 81.32 |
| EthylBenzene | 0 | 0 | 0 |
| Para-Xylene (PX) | 5.55 | 8.80 | 9.66 |
| Meta-Xylene (MX) | 0.54 | 0.57 | 0.58 |
| Ortho-Xylene (OX) | 0.48 | 0.47 | 0.47 |
| EthylToluene | 0.19 | 0.26 | 0.26 |
| TrimethylBenzene | 0.32 | 0.33 | 0.34 |
| C10+ | 0.09 | 0.18 | 0 |
| Toluene Conv., mole % | 6.79 | 9.87 | 10.72 |
| % PX in Total Xylenes | 84.47 | 89.43 | 90.20 |

[a]Based on toluene and methanol feed.

As can be seen from the data above, the catalyst showed approximately 10% toluene conversion and about 90% selectivity for p-xylene at relatively high LHSV and at a temperature of approximately 450° C.

Example 2

A catalyst charge of 3.0 ml was loaded in the reactor. The catalyst was dried at 200° C. under $H_2$ flow for at least 1 hour prior to feed introduction. The reactor pressure was maintained about 20 psig. The toluene/methanol premixed feed with a 2:1 mole ratio was introduced at a rate of 1.53 ml/min giving an LHSV of about 31 $hr^{-1}$. The cofeed $H_2$ was used at a rate of 0.11 mole $H_2$/mole of HC feed. Water was introduced with the hydrocarbon feed at start-up and maintained at 0.66 mole $H_2O$/mole HC feed. The run conditions and results are presented in Tables 2A and 2B below.

TABLE 2A

| Run Conditions | |
|---|---|
| Catalyst | Phosphoric Acid Treated ZSM-5, Non-Bound |
| Feed | 2:1 ratio |
| Start-up | LHSV 31, H2/HC 0.11, T = 500° C. |
| Run | LHSV 31, H2/HC 0.11, T = 500° C. |
| Water in feed | Started at same time of feed |

TABLE 2B

|  | Time on Stream, hour | | |
|---|---|---|---|
|  | 1.5 | 2.5 | 3.5 |
| Cat Bed Inlet Temp, ° C. | 510 | 503 | 508 |
| Inlet Pressure, psig | 20 | 20 | 20 |
| LHSV[a] | 30.6 | 30.6 | 30.6 |
| H2, mole/mole HC Feed | 011 | 0.11 | 0.11 |
| H2O, mole/mole HC Feed | 0.66 | 0.66 | 0.66 |
| Product Distribution, wt % | | | |
| C5– | 2.37 | 2.30 | 2.29 |
| Dimethylether | 0.93 | 0.41 | 0.25 |
| Methanol | 3.18 | 3.07 | 3.03 |
| Benzene | 0 | 0 | 0 |
| Toluene | 72.87 | 73.45 | 73.55 |
| EthylBenzene | 0 | 0 | 0 |
| Para-Xylene (PX) | 18.07 | 18.10 | 18.17 |
| Meta-Xylene (MX) | 0.90 | 0.90 | 0.91 |

TABLE 2B-continued

|  | Time on Stream, hour | | |
|---|---|---|---|
|  | 1.5 | 2.5 | 3.5 |
| Ortho-Xylene (OX) | 0.58 | 0.57 | 0.58 |
| EthylToluene | 0.38 | 0.39 | 0.38 |
| TrimethylBenzene | 0.56 | 0.54 | 0.54 |
| C10+ | 0.16 | 0.28 | 0.30 |
| Toluene Conv., mole % | 19.63 | 19.58 | 19.64 |
| % PX in Total Xylenes | 92.43 | 92.49 | 92.42 |

[a]Based on toluene and methanol feed.

As can be seen from the data above, the catalyst showed approximately a 20% toluene conversion and a greater than 90% selectivity for p-xylene while running at relatively high LHSV and at a temperature of approximately 500° C.

Example 3

A bound catalyst charge of 0.90 ml was loaded in the reactor, with 80% as active catalyst. The catalyst was dried at 200° C. under $H_2$ flow for at least 1 hour prior to feed introduction. The reactor pressure was maintained about 20 psig. The toluene/methanol premixed feed with a 2:1 mole ratio was introduced at a rate of 0.39 ml/min giving an LHSV of about 26 $hr^{-1}$. The cofeed $H_2$ was used at a rate of 0.11 mole $H_2$/mole of HC feed. Water was introduced with the hydrocarbon feed at start-up and maintained at 0.82 mole $H_2O$/mole HC feed. The run conditions and results are presented in Tables 3A and 3B below.

TABLE 3A

| Run Conditions | |
|---|---|
| Catalyst | Phosphoric Acid Treated ZSM-5, Alumina Bound |
| Feed | 2:1 ratio |
| Start-up | LHSV 26, H2/HC 0.11, T = 500° C. |
| Run | LHSV 26, H2/HC 0.11, T = 500° C. |
| Water in feed | Started at same time of feed |

TABLE 3B

|  | Time on Stream, hour | | |
|---|---|---|---|
|  | 1.6 | 2.6 | 4.1 |
| Cat Bed Inlet Temp, ° C. | 501 | 497 | 505 |
| Inlet Pressure, psig | 21 | 19 | 22 |
| LHSV[a] | 26.1 | 26.1 | 26.1 |
| H2, mole/mole HC Feed | 0.11 | 0.11 | 0.11 |
| H2O, mole/mole HC Feed | 0.82 | 0.82 | 0.82 |
| Product Distribution, wt % | | | |
| C5– | 2.35 | 2.20 | 2.32 |
| Dimethylether | 1.94 | 2.21 | 2.47 |
| Methanol | 13.44 | 9.20 | 8.28 |
| Benzene | 0 | 0 | 0 |
| Toluene | 75.59 | 79.48 | 80.17 |
| EthylBenzene | 0 | 0 | 0 |
| Para-Xylene (PX) | 5.63 | 5.57 | 5.47 |
| Meta-Xylene (MX) | 0.24 | 0.29 | 0.29 |
| Ortho-Xylene (OX) | 0.17 | 0.24 | 0.24 |
| EthylToluene | 0.20 | 0.24 | 0.21 |
| TrimethylBenzene | 0.16 | 0.22 | 0.20 |
| C10+ | 0.28 | 0.35 | 0.35 |
| Toluene Conv., mole % | 7.03 | 6.90 | 6.70 |
| % PX in Total Xylenes | 93.21 | 91.31 | 91.17 |

[a]Based on toluene and methanol feed.

The alumina bound ZSM-5 catalyst showed approximately 7% toluene conversion and greater than 90% selectivity for p-xylene while running at relatively high LHSV and at a temperature of approximately 500° C.

Example 4

A catalyst charge of 5.4 ml was loaded in the reactor. The catalyst was dried at 200° C. under $H_2$ flow for at least 1 hour prior to feed introduction. The reactor pressure was maintained about 20 psig. Different start-up and run conditions were used in this example. At start-up, the toluene/methanol premixed feed with a 2:1 mole ratio was introduced at a rate of about 3.1 ml/min giving an initial LHSV of about 34 $hr^{-1}$. The initial cofeed $H_2$ was used at a rate to give a $H_2$/HC mole ratio of about 0.10. After approximately 1.8 hours, run conditions were started wherein the toluene/methanol feed was adjusted to provide a LHSV of about 2 $hr^{-1}$ with a $H_2$/HC mole ratio of about 7–8. After the initial period, the hydrocarbon feed rate and cofeed $H_2$ were maintained generally constant. Water was introduced approximately 23 hours after start-up and its rates were varied (see Table 4B). The run conditions and results are presented in Tables 4A and 4B below and in FIG. 1.

TABLE 4A

| | Run Conditions |
|---|---|
| Catalyst | Phosphoric Acid Treated, Non-Bound |
| Feed | 2:1 ratio |
| Start-up | LHSV 34, H2/HC = 0.1, T 500° C. |
| Run | LHSV 2, H2/HC 7–8, T = 500° C. |
| Water in feed | Started after 23 h, varied during the run |

At start-up with no water feed, the initial toluene conversion and p-xylene selectivity were about 15% and 86%, respectively. As the LHSV and $H_2$/HC ratio were changed to run conditions, the p-xylene selectivity gradually decreased. Referring to FIG. 1, the amount of water added as cofeed varied in segments labeled A–E wherein:

A=no water
B=about 0.8 mole $H_2O$/mole HC feed
C=about 0.25 mole $H_2O$/mole HC feed
D=about 0.8 mole $H_2O$/mole HC feed
E=about 1.1 mole $H_2O$/mole HC feed When water was added at about 0.8 to 0.9 mole $H_2O$/mole of HC feed, the p-xylene selectivity increased dramatically. When the amount of water was reduced, to about 0.25 mole $H_2O$/mole of HC feed, the p-xylene selectivity decreased slightly, but increased when adjusted back to about 0.7 to 0.8 mole $H_2O$/mole HC feed.

Example 5

A catalyst charge of 4.1 ml was loaded in the reactor. The catalyst was dried at 200° C. under $H_2$ flow for at least 1 hour prior to feed introduction. The reactor pressure was maintained at about 20 psig. Different start-up and run conditions were used in this example. At start-up, the toluene/methanol feed with a 2:1 molar ratio was introduced at a rate of about 2.74 ml/min giving an initial LHSV of about 40 $hr^{-1}$. The initial cofeed $H_2$ was used at a rate to give a $H_2$/HC mole ratio of about 0.1. After approximately 2.5 hours, run conditions were started wherein the toluene/methanol feed was adjusted to provide a LHSV of about 2 $hr^{-1}$ with a $H_2$/HC mole ratio of about 7–8. Water was introduced approximately 2.5 hour after start-up and maintained at

TABLE 4B

| | Time on Stream, hour | | | | | | | | | | |
|---|---|---|---|---|---|---|---|---|---|---|---|
| | 1.8 | 27.3 | 123.3 | 171.3 | 291.3 | 380.8 | 507.3 | 549.8 | 668.8 | 699.8 | 819.3 |
| Cat Bed Inlet Temp, ° C. | 503 | 500 | 500 | 501 | 502 | 501 | 502 | 503 | 503 | 504 | 504 |
| Inlet Pressure, psig | 22 | 22 | 20 | 20 | 21 | 21 | 21 | 22 | 22 | 21 | 22 |
| LHSV[a] | 34.4 | 2.1 | 2.0 | 2.1 | 1.9 | 2.0 | 2.1 | 2.0 | 2.0 | 2.2 | 2.2 |
| H2, mole/mole HC Feed | 0.10 | 7.81 | 8.10 | 7.77 | 8.81 | 7.91 | 7.92 | 8.03 | 7.90 | 7.46 | 7.22 |
| H2O, mole/mole HC Feed | 0 | 0 | 0.81 | 0.78 | 0.87 | 0.25 | 0.25 | 0.75 | 0.75 | 0.70 | 1.13 |
| Product Distribution, wt % | | | | | | | | | | | |
| C5– | 1.39 | 2.37 | 1.86 | 2.97 | 2.01 | 1.68 | 1.75 | 1.63 | 1.68 | 1.88 | 2.63 |
| Dimethylether | 0.99 | 2.08 | 0.65 | 0.85 | 0.51 | 1.31 | 1.72 | 1.48 | 0.80 | 1.08 | 0.89 |
| Methanol | 2.49 | 4.58 | 3.41 | 3.72 | 3.06 | 4.65 | 6.11 | 4.80 | 4.92 | 4.74 | 5.31 |
| Benzene | 0 | 0 | 0 | 0 | 0 | 0 | 0 | 0 | 0 | 0 | 0 |
| Toluene | 79.39 | 75.78 | 72.90 | 72.45 | 72.65 | 76.05 | 76.38 | 74.81 | 74.51 | 74.25 | 73.64 |
| EthylBenzene | 0.07 | 0 | 0 | 0 | 0 | 0 | 0 | 0 | 0 | 0 | 0 |
| Para-Xylene (PX) | 11.29 | 11.21 | 17.38 | 16.60 | 17.99 | 12.44 | 10.47 | 13.56 | 14.36 | 14.49 | 14.44 |
| Meta-Xylene (MX) | 1.01 | 1.23 | 1.26 | 1.14 | 1.28 | 1.25 | 1.15 | 1.23 | 1.22 | 1.19 | 1.03 |
| Ortho-Xylene (OX) | 0.79 | 1.10 | 1.00 | 0.90 | 0.96 | 1.11 | 1.06 | 1.05 | 1.03 | 0.97 | 0.84 |
| EthylToluene | 0.35 | 0.21 | 0.27 | 0.24 | 0.28 | 0.21 | 0.17 | 0.21 | 0.22 | 0.22 | 0.20 |
| TrimethylBenzene | 0.78 | 1.20 | 1.13 | 1.01 | 1.11 | 1.11 | 1.02 | 1.06 | 1.11 | 1.04 | 0.89 |
| C10+ | 1.46 | 0.26 | 0.15 | 0.13 | 0.15 | 0.18 | 0.17 | 0.16 | 0.15 | 0.15 | 0.12 |
| Toluene Conv., mole % | 14.33 | 14.64 | 19.99 | 19.20 | 20.49 | 15.53 | 13.61 | 16.55 | 17.26 | 17.28 | 17.00 |
| % PX in Total Xylenes | 86.25 | 82.79 | 88.49 | 89.06 | 88.93 | 84.05 | 82.57 | 85.61 | 86.45 | 87.03 | 88.53 |

[a]Based on toluene and methanol feed.

0.6–0.7 mole $H_2O$/mole HC feed. The run conditions and results are presented in Tables 5A and 5B below and in FIG. 2.

TABLE 5A

Run Conditions

| | |
|---|---|
| Catalyst | Phosphoric Acid Treated ZSM-5, Non-Bound |
| Feed | 2:1 ratio |
| Start-up | LHSV 40, H2/HC = 0.1, T 500° C. |
| Run | LHSV 2, H2/HC 7–8, T = 500° C. |
| Water in feed | Started after 1 hour at 500° C. |

TABLE 5B

| | Time on Stream, hour | | | | | | |
|---|---|---|---|---|---|---|---|
| | 2.5 | 20.2 | 26.2 | 68.2 | 146.2 | 164.2 | 188.2 |
| Cat Bed Inlet Temp, ° C. | 503 | 506 | 503 | 502 | 500 | 500 | 502 |
| Inlet Pressure, psig | 24 | 19 | 22 | 21 | 21 | 20 | 21 |
| LHSV[a] | 40.2 | 2.1 | 2.0 | 2.1 | 2.0 | 2.0 | 2.1 |
| H2, mole/mole HC Feed | 0.09 | 7.55 | 7.89 | 7.72 | 8.08 | 7.71 | 7.70 |
| H2O, mole/mole HC Feed | 0 | 0.64 | 0.67 | 0.65 | 0.69 | 0.66 | 0.65 |
| Product Distribution, wt % | | | | | | | |
| C5– | 1.09 | 2.75 | 2.80 | 1.82 | 1.59 | 1.17 | 2.33 |
| Dimethylether | 0.42 | 0.76 | 1.03 | 0.56 | 0.31 | 0.46 | 0.62 |
| Methanol | 2.91 | 4.53 | 4.39 | 4.65 | 4.25 | 5.49 | 5.13 |
| Benzene | 0 | 0 | 0 | 0 | 0 | 0 | 0 |
| Toluene | 73.21 | 70.93 | 70.00 | 69.95 | 71.01 | 70.64 | 70.10 |
| EthylBenzene | 0.07 | 0 | 0 | 0 | 0 | 0 | 0 |
| Para-Xylene (PX) | 18.83 | 17.28 | 18.21 | 19.27 | 19.06 | 18.54 | 18.26 |
| Meta-Xylene (MX) | 1.23 | 1.28 | 1.26 | 1.31 | 1.31 | 1.27 | 1.24 |
| Ortho-Xylene (OX) | 0.79 | 0.94 | 0.87 | 0.91 | 0.92 | 0.92 | 0.87 |
| EthylToluene | 0.40 | 0.26 | 0.26 | 0.28 | 0.28 | 0.27 | 0.26 |
| TrimethylBenzene | 0.94 | 1.13 | 1.05 | 1.11 | 1.13 | 1.10 | 1.06 |
| C10+ | 0.11 | 0.15 | 0.13 | 0.13 | 0.14 | 0.13 | 0.13 |
| Toluene Conv., mole % | 20.83 | 20.32 | 21.13 | 22.07 | 21.69 | 21.31 | 21.14 |
| % PX in Total Xylenes | 90.30 | 88.64 | 89.57 | 89.65 | 89.49 | 89.42 | 89.62 |

[a]Based on toluene and methanol feed.

Figure 2:
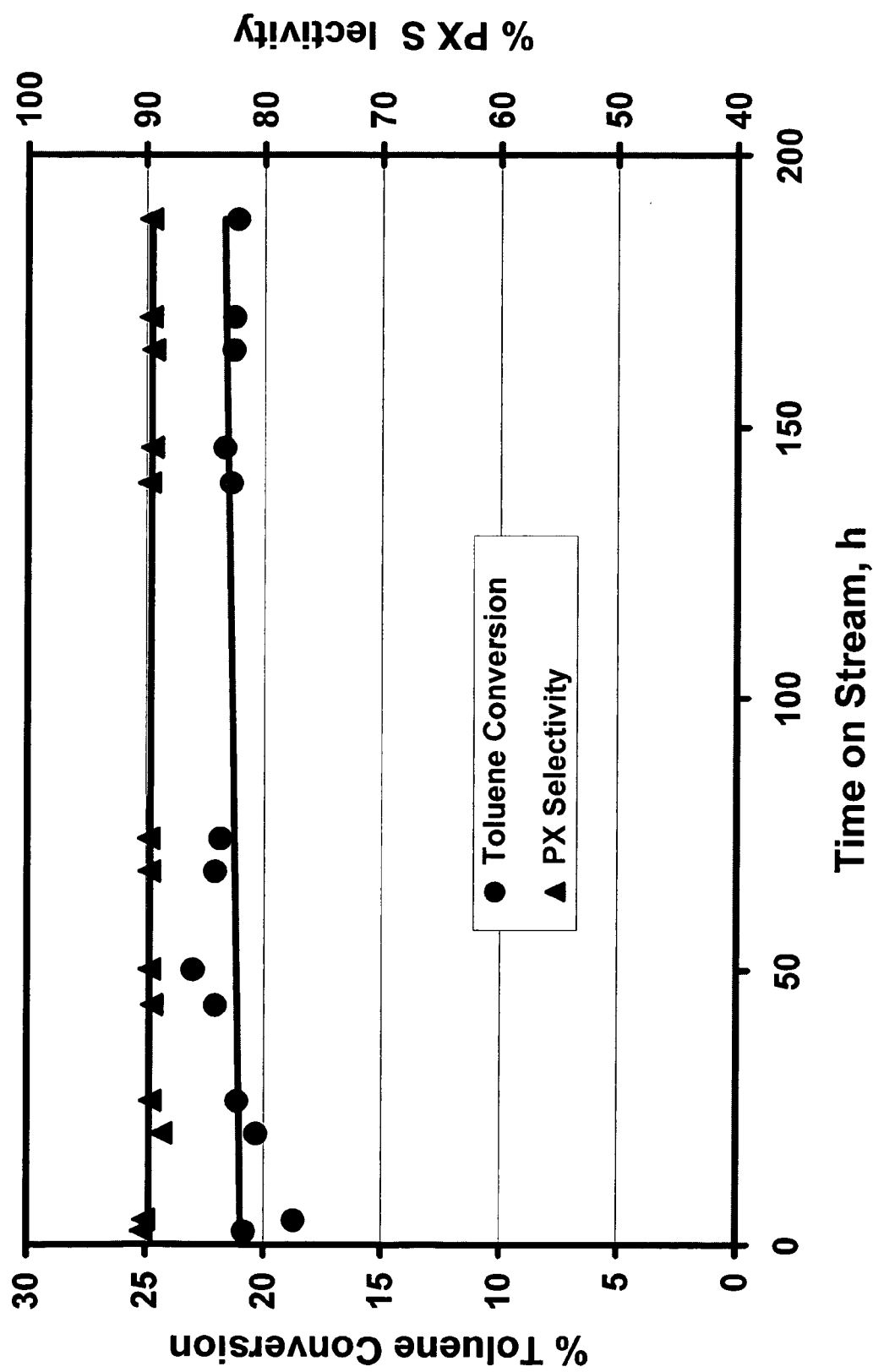
FIG. 2 is a plot of toluene conversion and para-xylene selectivity over time for the toluene methylation reaction of Example 5.

At start-up with no water feed, the initial toluene conversion and p-xylene selectivity were about 21% and 90%, respectively. Referring to FIG. 2, when water was added at 0.6–0.7 mole $H_2O$/mole HC feed, toluene conversion and p-xylene selectivity remained relatively stable, even after switching to run conditions.

Example 6

A catalyst charge of 5.4 ml was loaded in the reactor. The catalyst was dried at 200° C. under $H_2$ flow for at least 1 hour prior to feed introduction. The reactor pressure was maintained at about 20 psig. Different start-up and run conditions were used in this example. At start-up, the toluene/methanol feed at a 2:1 mole ratio was introduced at a rate of about 3.08 ml/min giving an initial LHSV of about 34 hr$^{-1}$. The initial cofeed $H_2$ was used at a rate to give a $H_2$/HC mole ratio of about 0.1. After approximately 2 hours, run conditions were started wherein the toluene/methanol feed was adjusted to provide a LHSV of about 2 hr$^{-1}$ with a $H_2$/HC mole ratio of about 7–8. Water was introduced approximately 124 hours after start-up and maintained at about 0.75 mole $H_2O$/mole HC feed. The run conditions and results are presented in Tables 6A and 6B below and in FIG. 3.

TABLE 6A

Run Conditions

| | |
|---|---|
| Catalyst | Phosphoric Acid Treated ZSM-5, Non-Bound |
| Feed | 2:1 ratio |
| Start-up | LHSV 34, H2/HC = 0.1, T 500° C. |
| Run | LHSV 2, H2/HC 7–8, T = 500–605° C. |
| Water in feed | Started after 124 hour at 500° C. |

TABLE 6B

| | Time on Stream, hour | | | | | | | |
|---|---|---|---|---|---|---|---|---|
| | 2.3 | 4.3 | 99.8 | 123.8 | 141.3 | 165.8 | 189.3 | 195.8 |
| Cat Bed Inlet Temp, ° C. | 500 | 502 | 500 | 501 | 500 | 501 | 543 | 605 |
| Inlet Pressure, psig | 22 | 21 | 21 | 22 | 20 | 22 | 24 | 21 |
| LHSV[a] | 34.3 | 2.0 | 2.1 | 2.1 | 2.0 | 2.0 | 2.1 | 2.1 |
| H2, mole/mole HC Feed | 0.11 | 7.94 | 7.66 | 7.91 | 7.92 | 7.92 | 7.79 | 7.74 |
| H2O, mole/mole HC Feed | 0 | 0 | 0 | 0 | 0.75 | 0.75 | 0.74 | 0.73 |
| Product Distribution, wt % | | | | | | | | |
| C5– | 2.14 | 1.30 | 0.90 | 1.54 | 1.73 | 1.79 | 1.43 | 1.38 |
| Dimethylether | 0.27 | 1.81 | 1.96 | 1.11 | 1.16 | 1.01 | 0.67 | 0.76 |
| Methanol | 1.93 | 4.96 | 4.83 | 3.02 | 5.22 | 4.29 | 3.83 | 2.87 |

TABLE 6B-continued

| | Time on Stream, hour | | | | | | | |
|---|---|---|---|---|---|---|---|---|
| | 2.3 | 4.3 | 99.8 | 123.8 | 141.3 | 165.8 | 189.3 | 195.8 |
| Benzene | 0 | 0 | 0 | 0 | 0 | 0 | 0 | 0 |
| Toluene | 72.63 | 72.64 | 77.02 | 79.69 | 73.16 | 72.90 | 70.88 | 72.75 |
| EthylBenzene | 0.07 | 0 | 0 | 0 | 0 | 0 | 0 | 0 |
| Para-Xylene (PX) | 17.60 | 14.57 | 9.37 | 8.94 | 13.21 | 14.28 | 17.05 | 16.97 |
| Meta-Xylene (MX) | 2.05 | 1.74 | 2.06 | 2.00 | 1.98 | 2.08 | 2.31 | 2.17 |
| Ortho-Xylene (OX) | 1.43 | 1.34 | 2.03 | 1.93 | 1.75 | 1.79 | 1.80 | 1.51 |
| EthylToluene | 0.34 | 0.25 | 0.11 | 0.11 | 0.16 | 0.18 | 0.13 | 0.08 |
| TrimethylBenzene | 1.36 | 1.24 | 1.47 | 1.42 | 1.42 | 1.47 | 1.71 | 1.34 |
| C10+ | 0.18 | 0.17 | 0.26 | 0.24 | 0.21 | 0.21 | 0.18 | 0.10 |
| Toluene Conv., mole % | 21.40 | 18.57 | 14.50 | 13.56 | 17.99 | 19.05 | 21.92 | 20.84 |
| % PX in Total Xylenes | 83.52 | 82.57 | 79.91 | 69.47 | 77.98 | 78.68 | 80.54 | 82.15 |

$^a$Based on toluene and methanol feed.

Figure 3:
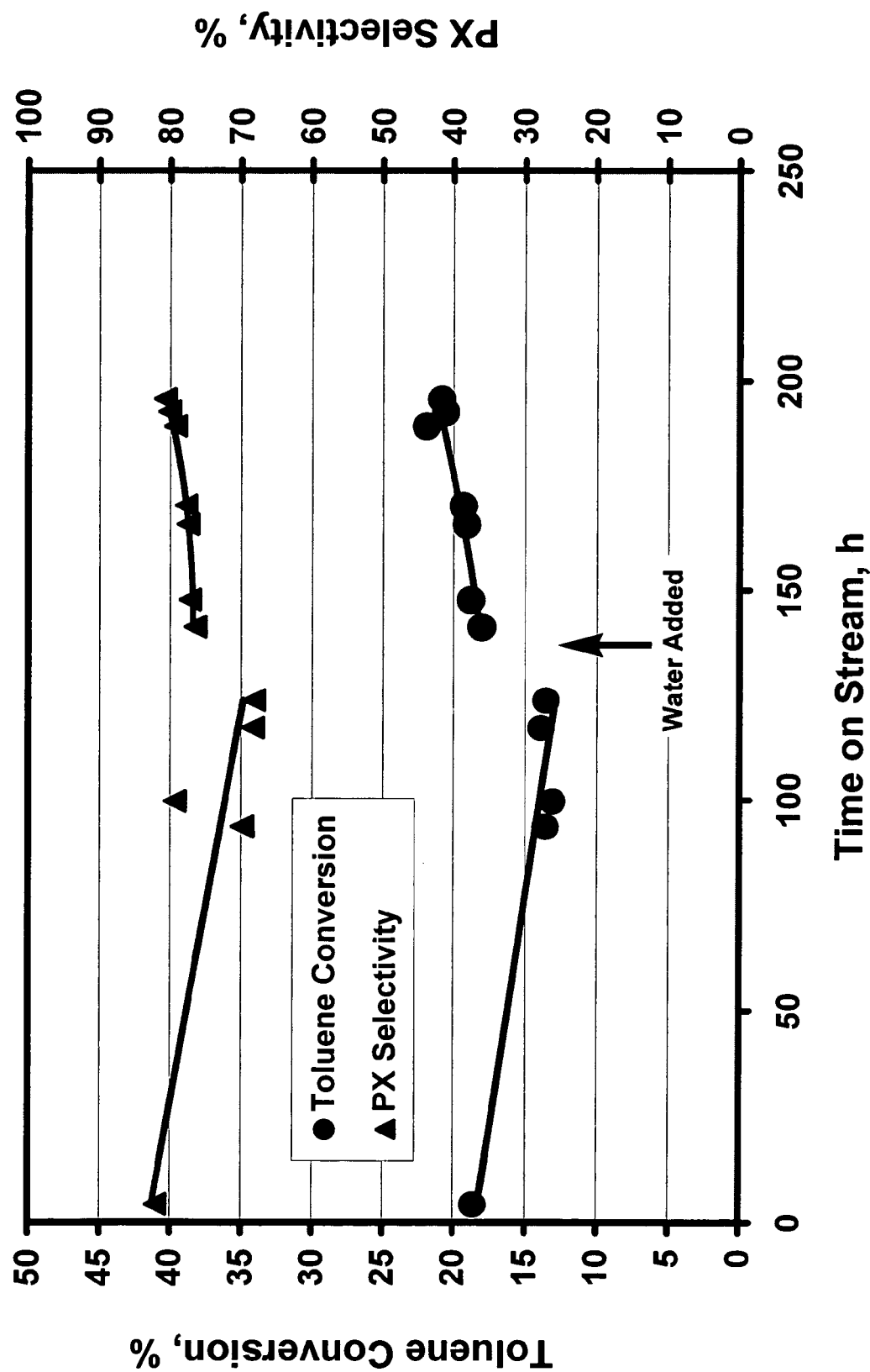
FIG. 3 is a plot of toluene conversion and para-xylene selectivity over time for the toluene methylation reaction of Example 6.

Referring to FIG. 3, as can be seen, conversion and p-xylene selectivity gradually decreased until water was added after 124 hours at about 0.75 mole H$_2$O/mole HC feed. Thereafter, toluene conversion and p-xylene selectivity continued to increase over time until the run was terminated.

Example 7

A catalyst charge of 5.4 ml was loaded in the reactor. The catalyst was dried at 200° C. under H$_2$ flow for at least 1 hour prior to feed introduction. The reactor pressure was maintained at about 20 psig. The toluene/methanol premixed feed with a 2:1 mole ratio. Different start-up and run conditions were used in this example. At start-up, the toluene/methanol feed at a 2:1 mole ratio was introduced at a rate of about 2.96 ml/min giving an initial LHSV of about 33 hr$^{-1}$. The initial cofeed H$_2$ was used at a rate to give a H$_2$/HC mole ratio of about 0.1. After approximately 2.5 hours, run conditions were started wherein the toluene/methanol feed was adjusted to provide a LHSV of about 2 hr$^{-1}$ with a H$_2$/HC mole ratio of about 7–8. Water was introduced approximately 2.5 hour after start-up and maintained at about 0.75 mole H$_2$O/mole HC feed. The reactor temperature was adjusted from about 500 to about 530° C. after about 195 hours. The run conditions and results are presented in Tables 7A and 7B below and in FIG. 4.

TABLE 7A

| Run Conditions | |
|---|---|
| Catalyst | Phosphoric Acid Treated ZSM-5, Non-Bound |
| Feed | 2:1 ratio |
| Start-up | LHSV 33, H2/HC = 0.1, T 500 ° C. |
| Run | LHSV 2, H2/HC 7–8, T = 500° C. |
| | (0–195 h), T = 525° C. (195–338 h) |
| Water in feed | Started after 1 hour at 500° C. |

TABLE 7B

| | Time on Stream, hour | | | | | | | | |
|---|---|---|---|---|---|---|---|---|---|
| | 2.5 | 20.2 | 43.7 | 74.2 | 170.2 | 212.2 | 236.2 | 314.2 | 331.7 |
| Cat Bed Inlet Temp, ° C. | 503 | 506 | 500 | 499 | 502 | 530 | 525 | 527 | 526 |
| Inlet Pressure, psig | 23 | 19 | 21 | 22 | 22 | 22 | 23 | 23 | 22 |
| LHSV$^a$ | 32.9 | 2.1 | 2.0 | 2.0 | 2.0 | 2.0 | 2.0 | 2.0 | 2.0 |
| H2, mole/mole HC Feed | 0.11 | 7.57 | 7.85 | 7.90 | 7.90 | 7.75 | 7.70 | 7.93 | 7.73 |
| H2O, mole/mole HC Feed | 0 | 0.73 | 0.76 | 0.76 | 0.78 | 0.75 | 0.76 | 0.77 | 0.75 |
| Product Distribution, wt % | | | | | | | | | |
| C5− | 0.97 | 1.73 | 1.81 | 1.66 | 2.79 | 1.77 | 1.30 | 1.08 | 1.43 |
| Dimethylether | 0.16 | 0.59 | 0.50 | 0.39 | 0.98 | 0.48 | 0.47 | 0.22 | 0.29 |
| Methanol | 2.75 | 5.39 | 5.03 | 4.47 | 4.86 | 4.44 | 4.51 | 3.94 | 4.58 |
| Benzene | 0 | 0 | 0 | 0 | 0 | 0 | 0 | 0 | 0 |
| Toluene | 76.11 | 71.29 | 70.25 | 69.88 | 69.39 | 72.89 | 68.63 | 68.29 | 68.67 |
| EthylBenzene | 0 | 0 | 0 | 0 | 0 | 0 | 0 | 0 | 0 |
| Para-Xylene (PX) | 15.44 | 16.20 | 17.45 | 18.33 | 16.94 | 16.24 | 19.82 | 20.87 | 19.84 |
| Meta-Xylene (MX) | 1.64 | 1.67 | 1.79 | 1.87 | 1.74 | 1.55 | 1.98 | 2.10 | 1.94 |
| Ortho-Xylene (OX) | 1.24 | 1.37 | 1.39 | 1.47 | 1.44 | 1.13 | 1.40 | 1.48 | 1.39 |
| EthylToluene | 0.32 | 0.21 | 0.23 | 0.25 | 0.23 | 0.13 | 0.20 | 0.22 | 0.20 |
| TrimethylBenzene | 1.18 | 1.35 | 1.37 | 1.48 | 1.44 | 1.21 | 1.52 | 1.62 | 1.49 |
| C10+ | 0.18 | 0.19 | 0.18 | 0.19 | 0.19 | 0.13 | 0.17 | 0.18 | 0.16 |
| Toluene Conv., mole % | 18.41 | 20.19 | 21.51 | 22.48 | 21.38 | 19.41 | 23.92 | 24.99 | 23.87 |
| % PX in Total Xylenes | 84.26 | 84.16 | 84.56 | 84.60 | 84.19 | 85.84 | 85.43 | 85.39 | 85.62 |

$^a$Based on toluene and methanol feed.

Figure 4:
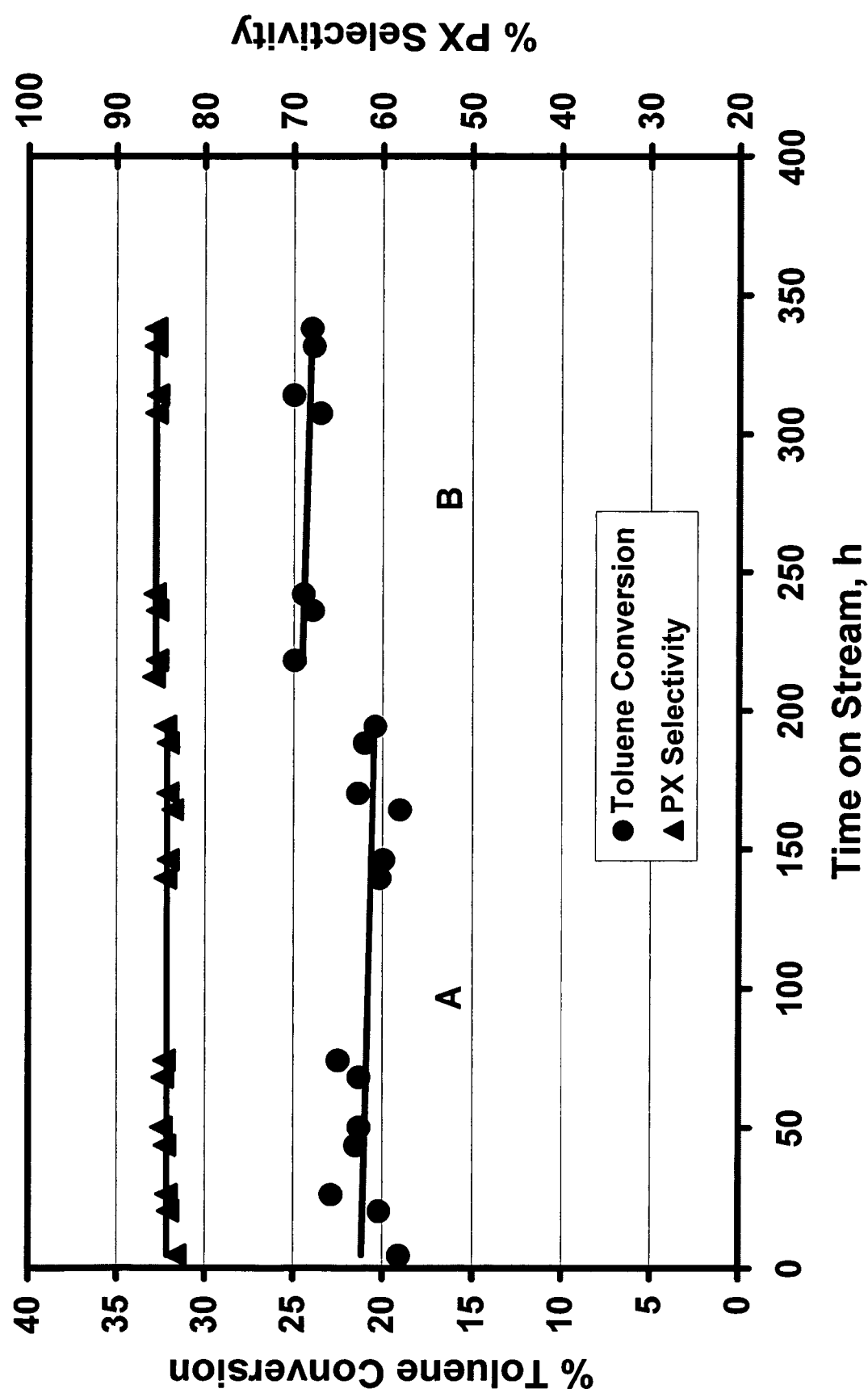
FIG. 4 is a plot of toluene conversion and para-xylene selectivity over time for the toluene methylation reaction of Example 7.

Referring to FIG. 4, after water was added 2.5 hours after start-up, toluene conversion and p-xylene selectivity remained steady throughout the run. In segments labeled A and B of FIG. 4, the catalyst bed inlet temperatures were maintained at about 500° C. and 525° C., respectively.

Example 8

A catalyst charge of 5.4 ml was loaded in the reactor. The catalyst was dried at 200° C. under $H_2$ flow for at least 1 hour prior to feed introduction. The reactor pressure was maintained about 20 psig. The toluene/methanol premixed feed with a 2:1 mole ratio was introduced at a rate of 0.46 ml/min giving an LHSV of about 5 $hr^{-1}$. The cofeed $H_2$ was used at a rate of 0.22 mole $H_2$/mole of HC feed. Water was introduced with the hydrocarbon feed at start-up and maintained at 5.45 mole $H_2O$/mole HC feed. The run conditions and results are presented in Tables 8A and 8B below.

TABLE 8A

| Run Conditions | |
|---|---|
| Catalyst | Phosphoric Acid Treated ZSM-5, Non-Bound |
| Feed | 2:1 ratio |
| Start-up | LHSV 5, H2/HC 0.22, T = 550° C. |
| Run | LHSV 5, H2/HC 0.22, T = 550° C. |
| Water in feed | Started at same time of feed |

TABLE 8B

| | Time on Stream, hour | |
|---|---|---|
| | 3.6 | 20.6 |
| Cat Bed Inlet Temp, ° C. | 551 | 552 |
| Inlet Pressure, psig | 23 | 22 |
| LHSV[a] | 5.1 | 5.1 |
| H2, mole/mole HC Feed | 0.22 | 0.22 |
| H2O, mole/mole HC Feed | 5.45 | 5.45 |
| Product Distribution, wt % | | |
| C5− | 1.44 | 0.97 |
| Dimethylether | 1.42 | 0.81 |
| Methanol | 5.69 | 5.78 |
| Benzene | 0 | 0 |
| Toluene | 75.11 | 74.49 |
| EthylBenzene | 0 | 0 |
| Para-Xylene (PX) | 14.00 | 15.42 |
| Meta-Xylene (MX) | 1.07 | 1.18 |
| Ortho-Xylene (OX) | 0.68 | 0.75 |
| EthylToluene | 0 | 0 |
| TrimethylBenzene | 0.59 | 0.60 |
| C10+ | 0 | 0 |
| Toluene Conv., mole % | 15.83 | 17.24 |
| % PX in Total Xylenes | 88.85 | 88.86 |

[a]Based on toluene and methanol feed.

As can be seen from the data above, the catalyst showed approximately a 16% toluene conversion and about 90% selectivity for p-xylene while running at LHSV of about 5 and at a temperature of approximately 550° C.

Comparative Example 9

A catalyst charge of 3.0 ml was loaded in the reactor. The catalyst was dried at 200° C. under $H_2$ flow for at least 1 hour prior to feed introduction. The reactor pressure was maintained at about 20 psig. In this example, start-up and run conditions were maintained the same and no water was added to feed. Toluene/methanol feed at a 2:1 mole ratio was introduced at a rate of about 1.55 ml/min giving a LHSV of about 31 $hr^{-1}$. The cofeed $H_2$ was used at a rate to give a $H_2$/HC mole ratio of about 0.75. The run conditions and results are presented in Tables 9A and 9B below.

TABLE 9A

| Run Conditions | |
|---|---|
| Catalyst | Phosphoric Acid Treated ZSM-5, Non-Bound |
| Feed | 2:1 ratio |
| Start-up | LHSV 31, H2/HC = 0.75, T 500° C. |
| Normal run | Same as start-up |
| Water in feed | None |

TABLE 9B

| | Time on Stream, hour | | | | |
|---|---|---|---|---|---|
| | 2.0 | 3.0 | 4.0 | 22.0 | 28.5 |
| Cat Bed Inlet Temp, ° C. | 502 | 503 | 500 | 499 | 498 |
| Inlet Pressure, psig | 21 | 22 | 22 | 22 | 23 |
| LHSV[a] | 31 | 31 | 31 | 31 | 31 |
| H2, mole/mole HC Feed | 0.75 | 0.75 | 0.75 | 0.76 | 0.75 |
| H2O, mole/mole HC Feed | 0 | 0 | 0 | 0 | 0 |
| Product Distribution, wt % | | | | | |
| C5− | 2.02 | 1.76 | 1.58 | 0.71 | 0.68 |
| Dimethylether | 1.49 | 1.74 | 1.79 | 1.49 | 2.24 |
| Methanol | 3.42 | 3.33 | 3.58 | 5.79 | 5.57 |
| Benzene | 0 | 0 | 0 | 0 | 0 |
| Toluene | 84.34 | 80.99 | 81.75 | 85.80 | 85.08 |
| EthylBenzene | 0 | 0 | 0 | 0 | 0 |
| Para-Xylene (PX) | 6.38 | 9.11 | 8.26 | 3.83 | 4.00 |
| Meta-Xylene (MX) | 0.81 | 1.09 | 1.08 | 0.85 | 0.87 |
| Ortho-Xylene (OX) | 0.73 | 0.92 | 0.94 | 0.80 | 0.82 |
| EthylToluene | 0.21 | 0.26 | 0.24 | 0.10 | 0.10 |
| TrimethylBenzene | 0.62 | 0.79 | 0.77 | 0.53 | 0.53 |
| C10+ | 0 | 0 | 0 | 0.11 | 0.11 |

TABLE 9B-continued

|  | Time on Stream, hour | | | | |
| --- | --- | --- | --- | --- | --- |
|  | 2.0 | 3.0 | 4.0 | 22.0 | 28.5 |
| Toluene Conv., mole % | 8.17 | 11.44 | 10.61 | 5.83 | 6.07 |
| % PX in Total Xylenes | 80.56 | 81.92 | 80.35 | 80.97 | 70.30 |

[a]Based on toluene and methanol feed.

As can be seen from the data above, the catalyst showed approximately 10% toluene conversion and greater than 80% selectivity for p-xylene during the first few hours but both toluene conversion and p-xylene selectivity declined after about 25 hours.

Example 10

A catalyst charge of 3.0 ml was loaded in the reactor. The catalyst was dried at 200° C. under $H_2$ flow for at least 1 hour prior to feed introduction. The reactor pressure was maintained at about 20 psig. In this example, the start-up and run conditions were maintained the same. Toluene/methanol feed at a 2:1 mole ratio was introduced at a rate of about 1.54 ml/min giving a LHSV of about 31 hr$^{-1}$. The cofeed $H_2$ was used at a rate to give a $H_2$/HC mole ratio of about 0.1. Water was introduced with the feed at about 0.65 mole $H_2O$/mole HC feed. In this example, combined $H_2$ and $H_2O$ rates were adjusted to give about 0.75 mole of total combined $H_2$ and $H_2O$ per mole of HC feed. This 0.75 mole cofeed/feed molar ratio was used in the preceding comparative example. The run conditions and results are presented in Tables 10A and 10B below.

TABLE 10A

| | Run Conditions |
| --- | --- |
| Catalyst | Phosphoric Acid Treated ZSM-5, Non-Bound |
| Feed | 2:1 ratio |

TABLE 10A-continued

| | Run Conditions |
| --- | --- |
| Start-up | LHSV 31, H2/HC = 0.1, T 500° C. |
| Normal run | Same as start-up |
| Water in feed | Started same time of HC feed |

TABLE 10B

|  | Time on Stream, hour | | | | | | |
| --- | --- | --- | --- | --- | --- | --- | --- |
|  | 2.2 | 3.0 | 4.0 | 21.0 | 27.5 | 45.5 | 51.5 |
| Cat Bed Inlet Temp, ° C. | 501 | 501 | 502 | 503 | 502 | 507 | 502 |
| Inlet Pressure, psig | 22 | 21 | 22 | 19 | 22 | 22 | 22 |
| LHSV[a] | 31 | 31 | 31 | 31 | 31 | 31 | 31 |
| H2, mole/mole HC Feed | 0.11 | 0.11 | 0.11 | 0.11 | 0.11 | 0.11 | 0.11 |
| H2O, mole/mole HC Feed | 0.65 | 0.65 | 0.65 | 0.65 | 0.64 | 0.66 | 0.66 |
| Product Distribution, wt % | | | | | | | |
| C5– | 3.06 | 2.89 | 3.02 | 1.80 | 1.57 | 1.13 | 1.49 |
| Dimethylether | 0.38 | 0.17 | 0.18 | 0.16 | 0.18 | 0.18 | 0.27 |
| Methanol | 7.93 | 1.09 | 1.43 | 3.13 | 2.08 | 1.84 | 2.58 |
| Benzene | 0 | 0 | 0 | 0 | 0 | 0 | 0 |
| Toluene | 66.27 | 71.33 | 70.99 | 73.19 | 73.53 | 76.31 | 75.91 |
| EthylBenzene | 0 | 0.07 | 0 | 0 | 0 | 0 | 0 |
| Para-Xylene (PX) | 19.77 | 21.57 | 21.55 | 19.06 | 19.84 | 17.96 | 17.17 |
| Meta-Xylene (MX) | 0.97 | 1.10 | 1.11 | 1.03 | 1.08 | 0.98 | 0.94 |
| Ortho-Xylene (OX) | 0.57 | 0.60 | 0.61 | 0.61 | 0.64 | 0.62 | 0.60 |
| EthylToluene | 0.36 | 0.41 | 0.41 | 0.36 | 0.39 | 0.36 | 0.36 |
| TrimethylBenzene | 0.69 | 0.77 | 0.69 | 0.65 | 0.67 | 0.62 | 0.59 |
| C10+ | 0 | 0 | 0 | 0 | 0 | 0 | 0.08 |
| Toluene Conv., mole % | 22.55 | 22.88 | 22.87 | 20.39 | 20.99 | 18.85 | 18.32 |
| % PX in Total Xylenes | 92.77 | 92.69 | 92.61 | 92.08 | 92.02 | 91.82 | 91.77 |

[a]Based on toluene and methanol feed.

As can be seen from the data above, the catalyst showed approximately 20% toluene conversion and a greater than 90% selectivity for p-xylene at relatively high LHSV and at a temperature of approximately 500° C. If these results are compared with the results from the comparative Example 9, it is clear that the use of steam in combination of $H_2$ was shown to be advantageous over the use of only $H_2$ as cofeed.

Example 11

A catalyst charge of 3.0 ml was loaded in the reactor. The catalyst was dried at 200° C. under $H_2$ flow for at least 1 hour prior to feed introduction. The reactor pressure was maintained at about 20 psig. In this example, the start-up and run conditions were maintained the same. Toluene/methanol feed at a 2:1 mole ratio was introduced at a rate of about 1.71 ml/min giving a LHSV of about 34 hr$^{-1}$. No cofeed $H_2$ was used in this example. Water was introduced with the feed at about 0.75 mole $H_2O$/mole HC feed. In the preceding example, the combined $H_2$ and $H_2O$ cofeed/feed molar ratio was around 0.75. The run conditions and results are presented in Tables 11A and 11B below.

TABLE 11A

| Run Conditions | |
|---|---|
| Catalyst | Phosphoric Acid Treated ZSM-5, Non-Bound |
| Feed | 2:1 ratio |
| Start-up | LHSV 34, H2/HC = 0, T 500° C. |
| Normal run | Same as start-up |
| Water in feed | Started same time of HC feed |

TABLE 11B

| | Time on Stream, hour | | | |
|---|---|---|---|---|
| | 2.1 | 3.1 | 4.1 | 21.6 |
| Cat Bed Inlet Temp, ° C. | 507 | 503 | 503 | 507 |
| Inlet Pressure, psig | 20 | 22 | 24 | 20 |
| LHSV[a] | 34 | 34 | 34 | 34 |
| H2, mole/mole HC Feed | 0 | 0 | 0 | 0 |
| H2O, mole/mole HC Feed | 0.75 | 0.75 | 0.75 | 0.75 |
| Product Distribution, wt % | | | | |
| C5– | 1.30 | 1.28 | 1.30 | 1.12 |
| Dimethylether | 0.19 | 0.19 | 0.20 | 0.21 |
| Methanol | 2.43 | 2.47 | 2.67 | 3.10 |
| Benzene | 0 | 0 | 0 | 0 |
| Toluene | 76.52 | 76.56 | 76.93 | 79.17 |
| EthylBenzene | 0 | 0 | 0 | 0 |
| Para-Xylene (PX) | 17.19 | 17.19 | 16.63 | 14.24 |
| Meta-Xylene (MX) | 0.90 | 0.88 | 0.86 | 0.82 |
| Ortho-Xylene (OX) | 0.54 | 0.53 | 0.52 | 0.54 |
| EthylToluene | 0.39 | 0.38 | 0.37 | 0.33 |
| TrimethylBenzene | 0.55 | 0.53 | 0.52 | 0.48 |
| C10+ | 0 | 0 | 0 | 0 |
| Toluene Conv., mole % | 18.08 | 18.03 | 17.49 | 15.16 |
| % PX in Total Xylenes | 92.27 | 92.42 | 92.39 | 91.28 |

[a] Based on toluene and methanol feed.

As can be seen from the data above, the catalyst showed approximately 18% toluene conversion and greater than 90% selectivity for p-xylene at relatively high LHSV and at a temperature of approximately 500° C. If these results are compared with the results from Example 10, the use of steam without $H_2$ cofeed showed the similar effect.

Example 12

A catalyst charge of 5.4 ml was loaded in the reactor. The catalyst was dried at 200° C. under $H_2$ flow for at least 1 hour prior to feed introduction. The reactor pressure was maintained at about 20 psig. Different start-up and run conditions were used in this example. At start-up, the toluene/methanol feed at a 2:1 mole ratio was introduced at a rate of about 3.06 ml/min giving an initial LHSV of about 34 $hr^{-1}$. The initial cofeed $H_2$ was used at a rate to give a $H_2$/HC mole ratio of about 0.1. After approximately 2 hours, run conditions were started wherein the toluene/methanol feed was adjusted to provide a LHSV of about 2 $hr^{-1}$ with a $H_2$/HC mole ratio of about 7–8. Water was introduced approximately 44 hours after start-up and its rate varied (see Table 12B). The reaction conditions and results are presented in Tables 12A and 12B below and in FIG. 5.

TABLE 12A

| Run Conditions | |
|---|---|
| Catalyst | Ammonium Hydrogen Phosphate Treated ZSM-5, Non-Bound |
| Feed | 2:1 ratio |
| Start-up | LHSV 34, H2/HC = 0.1, T 500° C. |
| Normal run | LHSV 2, H2/HC 7–8, T = 500° C. |
| Water in feed | Started after 44 h, varied during the run |

TABLE 12B

| | Time on Stream, hour | | | | | | | | | | |
|---|---|---|---|---|---|---|---|---|---|---|---|
| | 3.8 | 27.3 | 44.3 | 51.3 | 140.8 | 164.8 | 284.8 | 332.8 | 453.8 | 483.3 | 507.3 |
| Cat Bed Inlet Temp, ° C. | 504 | 502 | 502 | 503 | 503 | 502 | 503 | 503 | 504 | 507 | 503 |
| Inlet Pressure, psig | 19 | 22 | 22 | 20 | 19 | 20 | 21 | 23 | 20 | 23 | 20 |
| LHSV[a] | 2.1 | 2.1 | 2.1 | 2.0 | 2.1 | 2.1 | 2.0 | 2.1 | 2.1 | 2.1 | 2.1 |
| H2, mole/mole HC Feed | 0.11 | 7.56 | 7.92 | 7.96 | 7.89 | 7.89 | 8.04 | 7.97 | 7.85 | 7.84 | 7.96 |
| H2O, mole/mole HC Feed | 0 | 0 | 0 | 0.77 | 0.76 | 0.76 | 0.77 | 0.25 | 0.25 | 0.25 | 0.25 |
| Product Distribution, wt % | | | | | | | | | | | |
| C5– | 2.35 | 1.78 | 1.24 | 1.67 | 1.76 | 1.85 | 1.73 | 1.25 | 1.25 | 0.99 | 1.52 |
| Dimethylether | 4.60 | 3.31 | 3.05 | 1.65 | 1.81 | 1.83 | 1.44 | 2.22 | 2.88 | 2.48 | 3.73 |
| Methanol | 7.19 | 6.30 | 5.96 | 5.16 | 6.93 | 6.34 | 5.97 | 7.13 | 8.78 | 7.24 | 8.80 |
| Benzene | 0 | 0 | 0 | 0 | 0 | 0 | 0 | 0 | 0 | 0 | 0 |
| Toluene | 77.03 | 79.85 | 81.16 | 80.31 | 78.61 | 78.62 | 78.25 | 79.15 | 79.13 | 80.96 | 79.03 |
| EthylBenzene | 0 | 0 | 0 | 0 | 0 | 0 | 0 | 0 | 0 | 0 | 0 |
| Para-Xylene (PX) | 7.60 | 7.00 | 6.73 | 9.27 | 9.33 | 9.75 | 10.95 | 8.50 | 6.49 | 6.64 | 5.51 |
| Meta-Xylene (MX) | 0.33 | 0.50 | 0.54 | 0.54 | 0.43 | 0.44 | 0.48 | 0.52 | 0.44 | 0.51 | 0.43 |
| Ortho-Xylene (OX) | 0.26 | 0.44 | 0.47 | 0.47 | 0.35 | 0.37 | 0.41 | 0.44 | 0.39 | 0.45 | 0.39 |
| EthylToluene | 0.19 | 0.15 | 0.15 | 0.19 | 0.17 | 0.17 | 0.20 | 0.16 | 0.11 | 0.12 | 0.09 |
| TrimethylBenzene | 0.32 | 0.56 | 0.58 | 0.61 | 0.45 | 0.47 | 0.50 | 0.53 | 0.45 | 0.52 | 0.43 |

TABLE 12B-continued

| | Time on Stream, hour | | | | | | | | | |
|---|---|---|---|---|---|---|---|---|---|---|
| | 3.8 | 27.3 | 44.3 | 51.3 | 140.8 | 164.8 | 284.8 | 332.8 | 453.8 | 483.3 | 507.3 |
| C10+ | 0.13 | 0.12 | 0.12 | 0.12 | 0.17 | 0.15 | 0.08 | 0.10 | 0.08 | 0.10 | 0.08 |
| Toluene Conv., mole % | 8.97 | 8.60 | 8.32 | 10.70 | 10.64 | 11.05 | 12.19 | 10.02 | 7.96 | 8.11 | 7.00 |
| % PX in Total Xylenes | 92.73 | 88.23 | 86.95 | 90.16 | 92.29 | 92.34 | 92.51 | 89.87 | 88.72 | 87.47 | 87.07 |

[a]Based on toluene and methanol feed.

Figure 5:
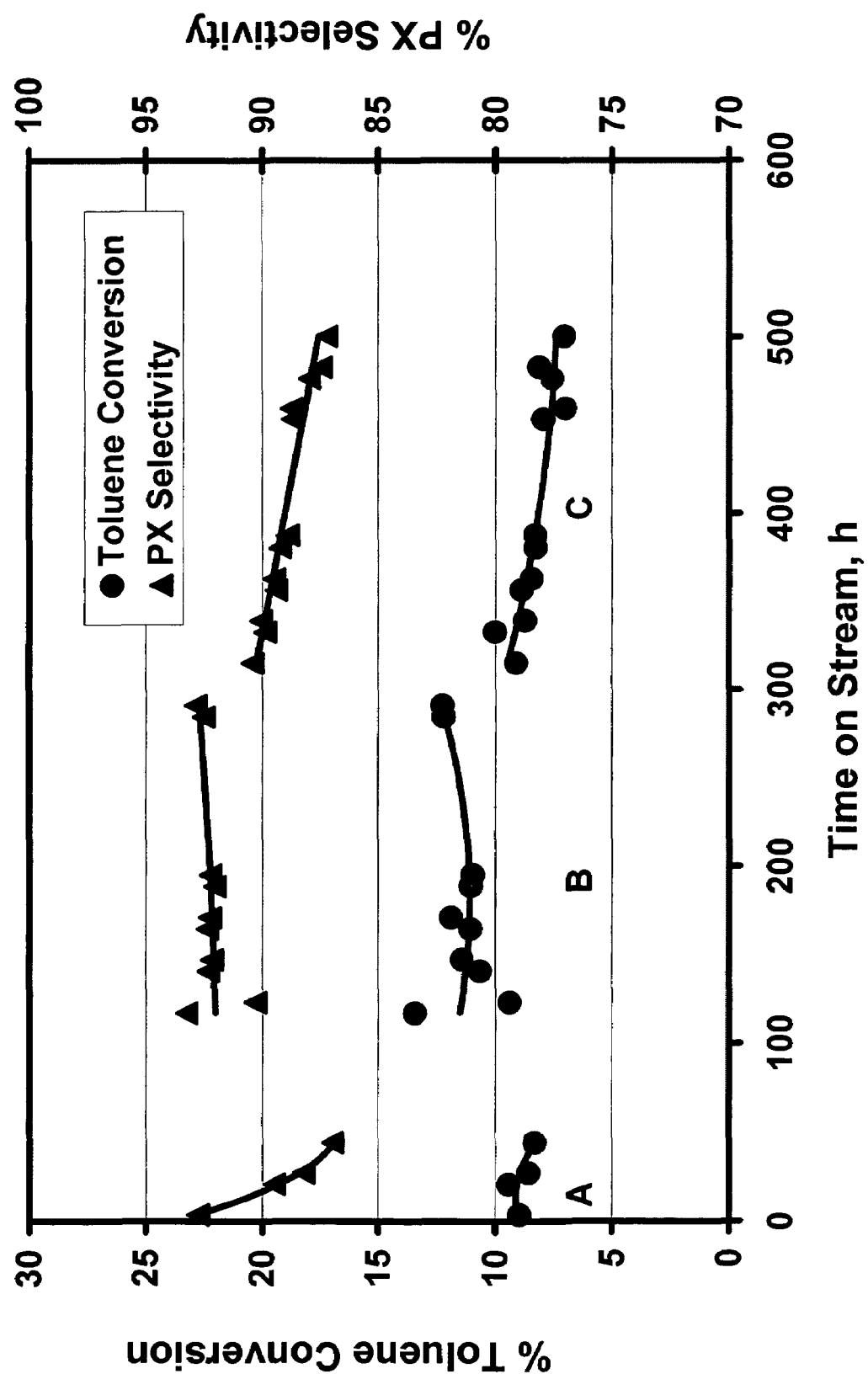
FIG. 5 is a plot of toluene conversion and para-xylene selectivity over time for the toluene methylation reaction of Example 12.

Referring to FIG. 5, the amount of water added as cofeed varied in segments labeled A–C wherein:
A=no water
B=about 0.8 mole $H_2O$/mole HC feed
C=about 0.25 mole $H_2O$/mole HC feed With no water in the feed, the initial toluene conversion and p-xylene selectivity were about 9% and 92%, respectively. After the LHSV and $H_2$/HC were adjusted to run conditions, the toluene conversion and p-xylene selectivity gradually decreased. After water was added, the toluene conversion and p-xylene selectivity increased. A decrease in toluene conversion and p-xylene selectivity was observed when the amount of water was reduced to 0.25 mole of $H_2O$ per mole of HC feed.

Spent Catalyst Analysis

Spent catalyst was analyzed to determine if it was structurally changed due to dealumination that may have occurred as a result of water formed during the toluene methylation reaction or from added water with the feed during the toluene methylation reaction. Magic angle spinning (MAS) solid state NMR studies were performed with the following instrument conditions: 400 MHz spectrometer ($^{27}$Al at 104.5 MHz), room temperature, silicon nitride rotors (Si3N4), 13 to 14 KHz sample spinning (about 800000 rpm), 10 degree tip to avoid saturation and 4000–10000 scans signal averaging. No proton decoupling was employed during testing. All spectra were referenced to aluminum chloride hexahydrate (run separately in a tube) at 0.0 ppm on the chemical shift scale. This leads to an internal reference of 104.85 ppm on the aluminum nitride (small impurity in the silicon nitride rotors).

The spent catalysts from Examples 4 and 12 were removed from the reactor after being used for more than 500 hours in the toluene methylation reaction using steam as cofeed. The catalysts were decoked by burning coke in air at 510° C. The catalyst was then analyzed by magic angle spinning (MAS) solid state NMR spectroscopy for $^{27}$Al.

Figure 6:
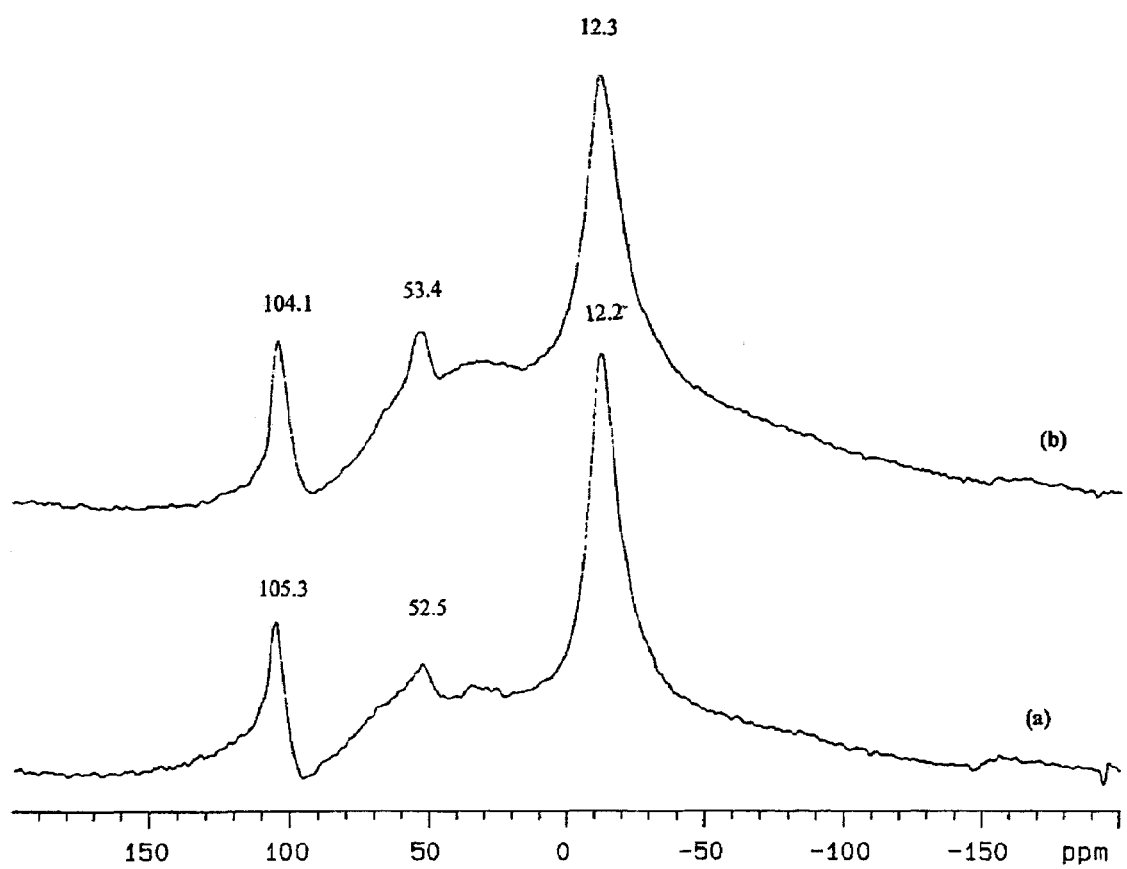
FIG. 6 shows $^{27}$Al MAS-NMR spectra for fresh AHP treated ZSM-5 and spent catalyst removed from reactor used in a toluene methylation reaction described in Example 12.

FIG. 6 shows the spectra of fresh and spent ammonium hydrogen phosphate (AHP) treated ZSM-5 catalysts from Example 12. The NMR spectrum of the fresh catalyst sample (spectrum a) shows structural tetrahedral aluminum peak in the 55–50 ppm region and is severely distorted, indicating presence of nested silanols caused by holes in the structure upon removal of some of the framework aluminum. The adjacent peak at 30–40 ppm, severely distorted, but still in the framework, is due to aluminum atoms likely either in the 3 or 5 coordination with oxygens. The biggest peak in the spectrum at −12 ppm is from octahedrally coordinated aluminum atoms.

In the case of the spent catalyst (spectrum b), the framework aluminum resonance at 53 ppm is much better defined than the fresh sample indicating some annealing of the defect structures may have taken place. Such annealing happens if the nested silanols condense to form Si—O—Si structures, which release the stress in the framework. The non-framework octahedral aluminum resonance at −12 ppm is again now the most intense and well defined resonance in the spectrum indicating a significant rehydration has occurred. This phenomenon is observed if water is part of the reaction mechanism. It can thus be seen that no appreciable difference was observed in strength of peak assigned to structural aluminum (tetrahedral Al) for the fresh and the spent catalyst samples.

Also, phosphoric acid (PA) treated ZSM-5 catalyst from Example 4 after removal from reactor was analyzed for $^{27}$Al NMR. As in the case of AHP treated catalyst, the spent PA-treated catalyst shows framework aluminum peak at 54 ppm (spectrum not shown). The 3- or 5-coordinated Al (broad resonance at 30–40 ppm) is significantly higher in intensity compared to the sample discussed above. There are 3 different octahedral (six coordinated) non-frame work aluminum species seen at −11 ppm and −20 ppm. They all appeared to be hydrated to some extent (Al with different numbers of water molecules coordinating).

From the MAS NMR spectroscopic study it is concluded that no appreciable difference was observed in strength of peak assigned to structural (tetrahedral Al) for the fresh and the spent catalyst samples. It is thus concluded that no structural aluminum loss from the zeolite occurred from the water formed during toluene methylation reaction or from added water with the feed.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of preparing a xylene product comprising:
    (a) providing a reactor containing a non-steamed, phosphorus-treated ZSM-5-type zeolite catalyst;
    (b) contacting the catalyst with a toluene/methanol feed and a cofeed of hydrogen under reactor conditions suitable for the methylation of toluene; and
    (c) introducing water cofeed into the reactor during the methylation reaction under conditions that provide substantially no structural aluminum loss of the catalyst from such introduction of water.

2. The method of claim 1, wherein:
    the cofeed water is introduced with the initial feed.

3. The method of claim 1, wherein:
    the cofeed water is introduced after the toluene methylation reaction has started.

4. The method of claim 1, wherein:
    the cofeed water is fed into the reactor at from about 0.2 mole to less than about 10 moles water per mole of toluene+methanol feed.

5. The method of claim 1, wherein:
the cofeed water is fed into the reactor at 0.3 mole to about 7 moles water per mole of toluene+methanol feed.

6. The method of claim 1, wherein:
the reactor has a catalyst bed inlet temperature maintained at less than 700° C.

7. The method of claim 1, wherein:
the phosphorus-treated ZSM-5-type zeolite catalyst has a total phosphorus content of from about 0.01 g P/g zeolite to about 0.15 g P/g zeolite.

8. The method of claim 1, wherein:
the method provides a xylene product having a para-xylene content of at least 80% by total moles of xylene.

9. The method of claim 1, wherein:
the toluene/methanol feed has a toluene/methanol molar ratio of from about 1:2 to about 10:1.

10. The method of claim 1, wherein:
the ZSM-5-type zeolite catalyst is treated with at least one of phosphoric acid and ammonium hydrogen phosphate.

11. The method of claim 1, wherein:
the reactor has a catalyst bed inlet temperature that is maintained from about 400° C. to about 600° C.

12. The method of claim 1, wherein:
the catalyst has a silica/alumina mole ratio prior to phosphorus treatment from about 25 to about 300.

13. The method of claim 1, wherein:
the catalyst is a bound catalyst.

14. A method of preparing a xylene product comprising:
providing a fixed-bed reactor containing a non-steamed, phosphorus-treated ZSM-5-type zeolite catalyst having a total phosphorus content of from about 0.01 g P/g zeolite to about 0.15 g P/g zeolite and a silica/alumina mole ratio prior to phosphorus treatment from about 25 to about 300;

contacting the catalyst with a toluene/methanol feed and a cofeed of hydrogen under reactor conditions suitable for the methylation of toluene; and introducing water into the reactor during the methylation reaction in an amount of from about 0.2 to less than about 10 moles of water per mole toluene+methanol under conditions that provide substantially no structural aluminum loss of the catalyst from such introduction of water to produce a xylene product having a para-xylene content of at least 80% by total moles of xylene and wherein the catalyst bed inlet temperature is less than 700° C.

15. The method of claim 14, wherein:
the water is introduced with the initial toluene/methanol feed.

16. The method of claim 14, wherein:
the water is introduced after the toluene methylation reaction has started.

17. The method of claim 14, wherein:
the water is fed into the reactor at a ratio of from about 0.3 to about 7 moles per mole of toluene+methanol.

18. The method of claim 14, wherein:
the toluene/methanol feed has a toluene/methanol molar ratio of from about 1:2 to about 10:1.

19. The method of claim 14, wherein:
the ZSM-5-type zeolite catalyst is treated with at least one of phosphoric acid and ammonium hydrogen phosphate.

20. The method of claim 14, wherein:
the reactor has a catalyst bed inlet temperature that is maintained from about 400° C. to about 700° C.

21. The method of claim 14, wherein:
the catalyst is a bound catalyst.

* * * * *